(12) United States Patent
Bloomquist et al.

(10) Patent No.: US 7,647,821 B2
(45) Date of Patent: Jan. 19, 2010

(54) APPARATUS FOR ESTIMATING THE RATE OF EROSION AND METHODS USING THE SAME

(76) Inventors: David G. Bloomquist, 11714 SW. 89th St., Gainesville, FL (US) 32608; Donald Max Sheppard, 1656 NW. 22nd Cir., Gainesville, FL (US) 32605

( * ) Notice: Subject to any disclaimer, the term of this patent is extended or adjusted under 35 U.S.C. 154(b) by 75 days.

(21) Appl. No.: 12/053,936

(22) Filed: Mar. 24, 2008

(65) Prior Publication Data

US 2009/0000361 A1    Jan. 1, 2009

Related U.S. Application Data

(63) Continuation of application No. PCT/US2006/037349, filed on Sep. 22, 2006.

(60) Provisional application No. 60/719,773, filed on Sep. 22, 2005.

(51) Int. Cl.
*G01N 17/00* (2006.01)
(52) U.S. Cl. .......................................... 73/86; 73/865.6
(58) Field of Classification Search ............... 73/86, 73/865.6, 760, 788, 847
See application file for complete search history.

(56) References Cited

U.S. PATENT DOCUMENTS 6,269,684 B1 * 8/2001 Maki et al. ................. 73/53.01

FOREIGN PATENT DOCUMENTS

| EP | 0279182 | 8/1988 |
|---|---|---|
| GB | 2162952 | 2/1986 |
| JP | 61030747 | 2/1986 |

OTHER PUBLICATIONS

Robert P. Chapuis, Use of Rotational Erosion Device on Cohesive Soils, Journal, 1986, pp. 23-28, Transportation Research Record.
Jiang et al., Estimation of Contraction Scour in Riverbed Using SERF, Journal, Jul./Aug. 2004, pp. 215-218, vol. 130, No. 4, Journal of Waterway, Port, Coastal and Ocean Engineering.
Arulanandan et al., Pore and Eroding Fluid Influences on Surface Erosion of Soil, Journal, Jan. 1975, pp. 51-66, vol. 101, No. 1, Journal of the Geotechnical Engineering Division.
International Search Report from PCT/US2006/037349 dated Apr. 5, 2007.

* cited by examiner

*Primary Examiner*—Hezron Williams
*Assistant Examiner*—Nathaniel Kolb
(74) *Attorney, Agent, or Firm*—Alston & Bird LLP

(57) ABSTRACT

Various embodiments of the invention comprise devices, systems, and methods for estimating the rate at which rock, soil or any self-supporting material erode. Particular embodiments of the invention relate to devices and systems that subject a stationary soil or rock sample to shear stresses by rotating fluid about the soil or rock sample to simulate the effects of flowing fluids on the soil or rock sample. In various embodiments, the devices and systems include a torque cell unit and clutch assembly.

42 Claims, 13 Drawing Sheets

APPARATUS FOR ESTIMATING THE RATE OF EROSION AND METHODS USING THE SAME

CROSS REFERENCE TO RELATED APPLICATIONS

This application is a continuation of PCT/US2006/037349, filed Sep. 22, 2006, which claims priority from U.S. Provisional Application No. 60/719,773, filed Sep. 22, 2005, the contents of both of which are hereby incorporated by reference in their entirety.

BACKGROUND OF THE INVENTION

1. Field of the Invention

This invention relates to devices, systems, and methods for estimating the rate at which rock and soil erode and, more specifically, to devices that subjects a soil or rock sample to shear stresses applied by rotating fluid about the sample to simulate the effects of flowing fluids on the soil or rock sample and to systems and methods using the same.

2. Background of the Related Art

The ability of rock or soil ("media") to support relatively large structural loads depends on many factors, which can include the type of medium, the mineralogy of the medium, the strength of the medium (e.g., shear strength and compressive strength), the bearing capacity of the medium, the extent of weathering or fracturing or the like. For example, soil medium such as a hard glacial till or a stiff over-consolidated clay can be excellent load-carrying medium; whereas, soil medium such as organic clays, expansive clays, soft, unconsolidated clays or submerged silts are totally unsuitable. Similarly, rock medium such as fresh, unweathered granite that is not highly fractured can be an excellent load-carrying medium; whereas, clayey shales, chalks, porous or karstic limestone, friable sandstones or even a heavily weathered, highly fractured granite can be totally unsuitable.

In a marine environment, especially in a marine environment having relatively fast moving water ("fluid"), the ability of the medium to support loads is further complicated by the erosion or scour caused by the moving fluid. Indeed, when a fluid flows over an erodable soil, e.g., sand, silt, clay, soft rock, highly erodable rock or the like, at sufficient velocity, the medium can be eroded completely or can be eroded sufficiently to lose some of its strength or load-carrying capability. As a result, when designing foundations for structures, e.g., piers, caissons, piles, pressure-injected piles or the like, in a marine environment, e.g., a river, stream, coastline or the like, it would benefit the engineer or architect making the design to know the long- and short-term effects of the flowing fluid on the medium at the medium-foundation interface. As an example, the penetration depth of a bridge pier foundation that is to be located in and supported by the sediment requires knowledge of how much the channel bed will be lowered during a design flow event.

This is especially true when a foundation element 10 is socketed into the medium 5 (FIG. 1) so that the medium 5 itself supports some of or a considerable portion of the total load through side friction 6. The findings of Osterberg and Gill in "Load transfer mechanism for piers socketed into hard soils and rock" from the Proceedings of the $9^{th}$ Canadian Symposium on Rock Mechanics, pp. 235-262 (1973) are fully incorporated herein by reference.

Presently, there are only a few field tests available for testing in situ bond strength between a foundation element 10 and a medium 5. The preferred or most widely practiced test is the "field pull-out test", which is a destructive, relatively expensive test. During a field pull-out test, a foundation element 10, e.g., a pile, is installed, e.g., socketed, into the medium 5 according to the design specifications. Subsequently, a tensile load 3 is applied to the free end 2 of the foundation element 10 to pull the foundation element 10 from its socket 8. Alternatively, a hydraulic jack is placed beneath the foundation element and jacked upwards, creating shear stresses along the perimeter of the foundation element 10. Field instruments, e.g., stress-strain gauges or the like, typically, are placed at discrete locations along the length of the end portion 4 of the foundation element 10 that will be buried in the socket 8. As a pull-out or jacking load 3 is applied to the free or embedded end 2 of the foundation element 10, stress and strain measurements can be recorded from which engineers can estimate an in situ shear strength of the medium 5. Engineers can then use the results of the test to refine their design assumptions and re-design as necessary.

Others have developed empirical relationships for estimating field strength based on results of laboratory testing. For example, the shear strength ($\tau$) of a medium socket can be estimated based on an unconfined compression test (q, test) using the following formula and a suitable factor of safety:

$$\tau = q_u/20$$

There are no known direct measurement tests, however, that simulate the 5 impact of the environment, i.e., the erosive effects of the flowing fluid, and time on the medium and, hence, the foundation.

Accordingly, it would be desirable to provide devices, systems, and laboratory testing methods for estimating the rate of medium erosion. Moreover, it would be desirable to provide devices, systems, and laboratory testing methods for measuring the rate of medium erosion by rotating an outer cylinder portion about a fixed, non-rotating sample of the medium, wherein the rotation of the outer cylinder portion causes a fluid to replicate fluid flow over the surface of the medium sample.

SUMMARY OF THE INVENTION

In a first embodiment, the present invention provides a system for evaluating a rate of erosion of a medium sample subject to shear stresses generated by movement of a fluid. Preferably, the system comprising a rotating erosion testing apparatus; a vertical support portion for supporting and stabilizing the support portion and the torque cell unit of the rotating erosion testing apparatus; a horizontal support portion, having an axis of rotation, for supporting and providing rotation to the rotating portion and to the fluid contained therein; and a control unit for controlling the torque or shear stress applied to the rotating portion and the medium sample. More preferably, the rotating erosion testing apparatus includes a rotating portion that contains a fluid for providing a desired torque or a desired shear stress to the medium sample through the fluid; a support portion for supporting and stabilizing the medium sample during testing, that can be inserted into and removed from the upper opening of the rotating portion to a desired position in said rotating portion; and a torque cell and clutch unit for measuring an operating torque imparted to the medium sample disposed on the support portion.

In one aspect of the first embodiment, the medium is a core sample of rock or a core sample of a hard or stiff cohesive soil and the fluid is selected from the group consisting of fresh water, salt water, oil, an acidic solution, a saline solution, a slurry mixture, glycerin, and any liquid exhibiting high viscosity. In another aspect of the first embodiment, the sample-supporting portion includes a supporting rod having a diameter that is slight less than a diameter of an opening drilled or bored through the center of the medium sample; a top platen, having a central opening that is structured and arranged to be slightly larger in diameter than the diameter of the support rod, for frictionally engaging an upper end of the media sample; a bottom platen, having a central opening that is structured and arranged to be slightly larger in diameter than the diameter of the support rod, for frictionally engaging a lower end of the media sample; and a pair of securing devices for releasably securing the top platen and the bottom platen so that the medium sample is rigidly confined between the top and bottom platens.

In yet another aspect of the first embodiment, the torque cell and clutch unit comprises an upper clutch slip mechanism that is in operational association with a strain gage that is structured and arranged on a torque arm; and a lower clutch assembly that is in operational association with the medium sample. In a preferred embodiment, the upper clutch slip mechanism can be set with a predetermined torque so that when a torque that is greater than the predetermined torque is applied to the lower clutch assembly, the testing apparatus will shut down to stop the torque applied to said lower clutch assembly. Preferably, a strain gage that is structured and arranged on a torque arm for providing strain data that can be used to evaluate the shear stress applied to the medium sample by the rotating fluid. More preferably, the torque cell and clutch unit further comprises a mechanical stop that is structured and arranged in operational association with the torque arm so that if a torque that is greater than the predetermined torque is applied to the lower clutch assembly but the testing apparatus does not shut down, the mechanical stop will cause the testing apparatus to shut down.

In a second embodiment, the present invention discloses a testing apparatus for subjecting a medium sample to a moving fluid to evaluate a rate of erosion of the medium sample due to shear stresses generated by the moving fluid. Preferably, the apparatus comprises a rotating portion, that contains a fluid for providing a desired torque or a desired shear stress to the medium sample through the fluid; a sample-supporting portion for supporting and stabilizing the medium sample during testing, that can be inserted into and removed from the upper opening of the rotating portion to a desired position in said rotating portion; and a torque cell and clutch unit for measuring an operating torque imparted to the medium sample disposed on the support portion.

In one aspect of the second embodiment, the medium is a core sample of rock or a core sample of a hard or stiff cohesive soil and the fluid is selected from the group consisting of fresh water, salt water, oil, an acidic solution, a saline solution, a slurry mixture, glycerin, and any liquid exhibiting high viscosity.

In another aspect of the second embodiment, the sample-supporting portion includes a supporting rod having a diameter that is slight less than a diameter of an opening drilled or bored through the center of the medium sample; a top platen, having a central opening that is structured and arranged to be slightly larger in diameter than the diameter of the support rod, for frictionally engaging an upper end of the media sample; a bottom platen, having a central opening that is structured and arranged to be slightly larger in diameter than the diameter of the support rod, for frictionally engaging a lower end of the media sample; and a pair of securing devices for releasably securing the top platen and the bottom platen so that the medium sample is rigidly confined between the top and bottom platens.

In yet another aspect of the second embodiment, the torque cell and clutch unit comprises an upper clutch slip mechanism that is in operational association with a strain gage that is structured and arranged on a torque arm; and a lower clutch assembly that is in operational association with the medium sample. In a preferred embodiment, the upper clutch slip mechanism can be set with a predetermined torque so that when a torque that is greater than the predetermined torque is applied to the lower clutch assembly, the testing apparatus will shut down to stop the torque applied to said lower clutch assembly. Preferably, a strain gage that is structured and arranged on a torque arm for providing strain data that can be used to evaluate the shear stress applied to the medium sample by the rotating fluid. More preferably, the torque cell and clutch unit further comprises a mechanical stop that is structured and arranged in operational association with the torque arm so that if a torque that is greater than the predetermined torque is applied to the lower clutch assembly but the testing apparatus does not shut down, the mechanical stop will cause the testing apparatus to shut down.

In a third embodiment, the present invention discloses a method of testing and evaluating a rate of erosion of a medium sample subject to shear stresses generated by movement of a fluid. Preferably, the method comprises providing a rotating erosion testing apparatus that includes a rotating portion, having an upper opening, that contains a fluid for providing a desired torque or a desired shear stress to the medium sample through the fluid, a support portion for supporting and stabilizing the medium sample during testing, that can be inserted into and removed from the upper opening of the rotating portion to a desired position in said rotating portion, and a torque cell and clutch unit for measuring an operating torque imparted to the medium sample disposed on the support portion; applying rotational energy to the rotating portion of the rotating erosion testing apparatus for a predetermined period of time; measuring strain that is applied to the medium sample by the fluid in the rotating portion; measuring an amount of weight loss or volume loss of the medium sample at the end of the predetermined period of time; and calculating a rate of erosion based on the weight loss or volume loss of the medium sample and said predetermined period of time.

In one aspect of the third embodiment, the method further includes controlling the rotational energy applied to the rotating portion of the rotating erosion testing apparatus using strain data.

In another aspect of the third embodiment, the method further includes monitoring a torque applied to the medium sample; comparing the monitored torque with an allowable torque; and interrupting the rotational energy applied to the rotating portion of the rotating erosion testing apparatus when the monitored torque exceeds the allowable torque and/or monitoring a strain applied to the medium sample; comparing the monitored torque with an allowable strain; and interrupting the rotational energy applied to the rotating portion of the rotating erosion testing apparatus when the monitored strain exceeds the allowable strain.

BRIEF DESCRIPTION OF THE DRAWINGS

The invention will be better understood by reference to the following more detailed description and accompanying drawings where like reference numbers refer to like parts.

DETAILED DESCRIPTION OF THE INVENTION INCLUDING PREFERRED EMBODIMENTS

Figure 1:
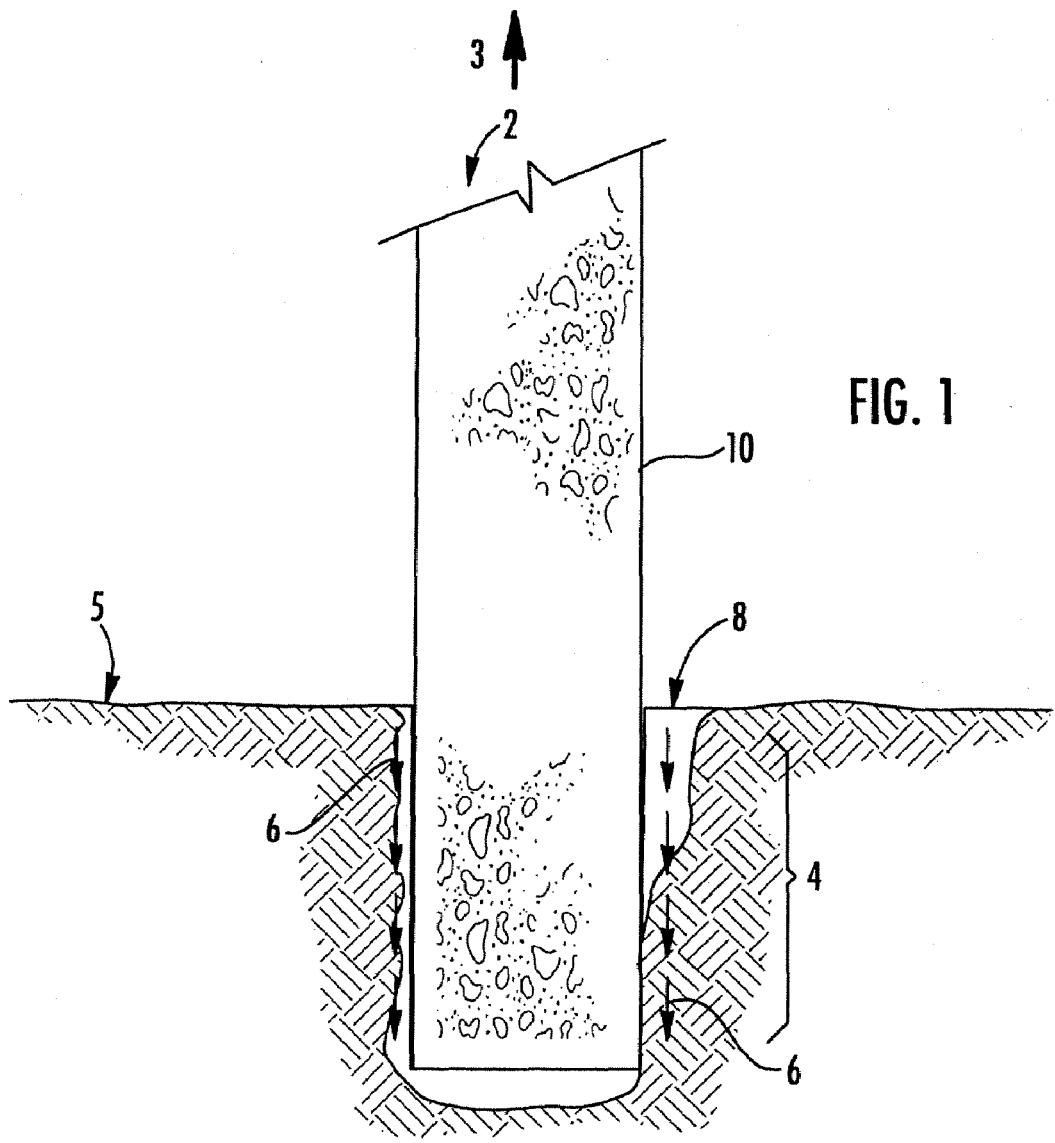
FIG. 1 is a diagrammatic of foundation element socketed into a medium.
Figure 2:
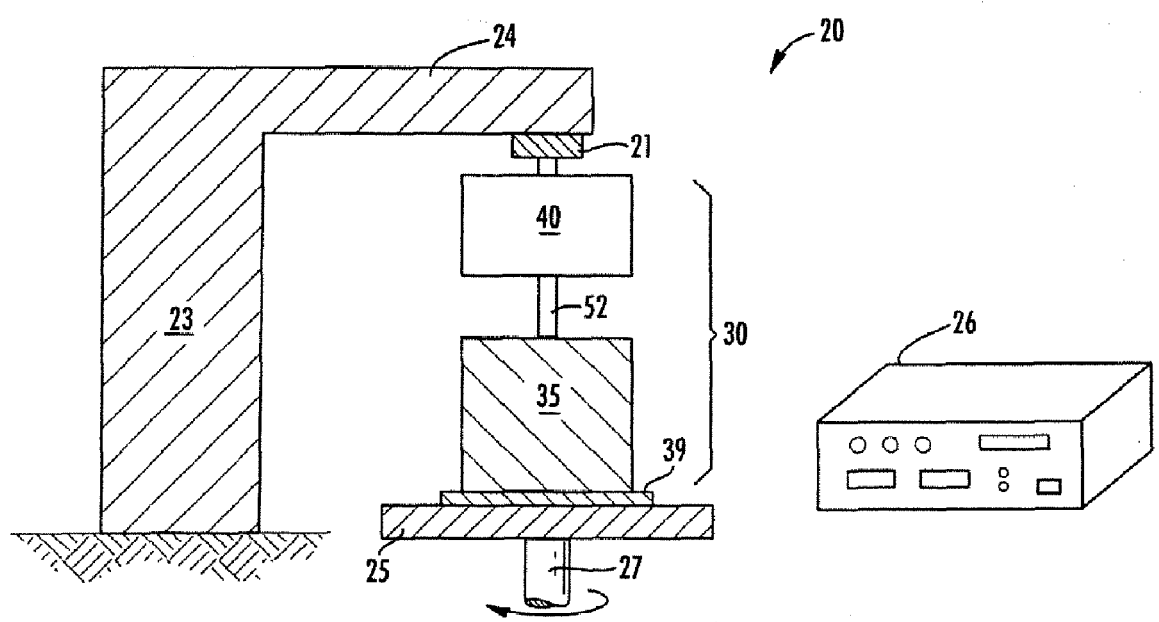
FIG. 2 is an illustrative embodiment of a system for performing testing to evaluate the rate of erosion of a medium sample in accordance with the present 5 invention.
Figure 3:
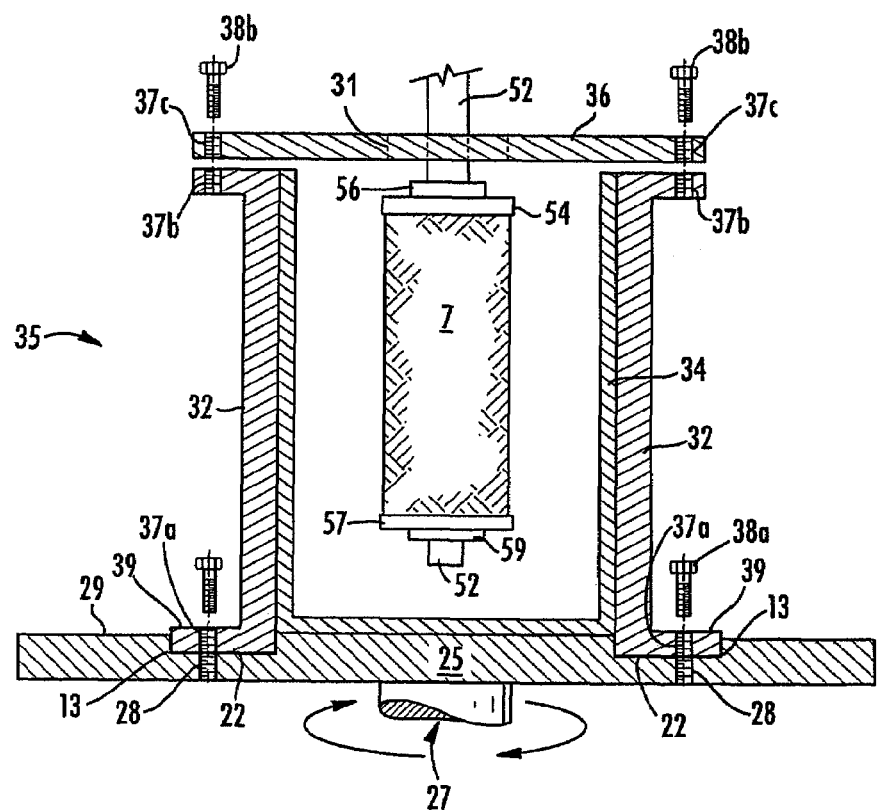
FIG. 3 is an illustrative embodiment of a Rotating Erosion Testing Apparatus ("RETA") in accordance with the present invention.

Referring to FIGS. 2 and 3, systems 20 for testing a medium sample to evaluate the rate of erosion of the medium sample when subject to shear stresses generated by fluid flow will be described. In a preferred embodiment, the system 20 comprises a Rotating Erosion Test Apparatus (RETA) 30, a fixed or stationary, vertical support portion 23 to support and provide stability to the non-rotating portions of the RETA 30, a rotatable horizontal support portion 25 that supports and rotates the rotating portion 35 of the RETA 30, and a control unit 26.

The Rotating Erosion Test Apparatus

In a preferred embodiment, the RETA 30 comprises a rotating portion 35 and a non-rotating portion. The non-rotating portion further includes a torque cell unit 40 and support portion 50. In a preferred embodiment, the rotating portion 35 of the RETA 30 is removably, secured to the upper surface 29 of the rotatable horizontal support portion 25. The rotatable horizontal support portion 25 is in operational communication with a rotor element 27 that can be rotated at a desired speed ("RPM"), e.g., by a motor or a machine (not shown), to provide a desired torque to the rotating portion 35 of the RETA 30.

In one aspect of the present invention, the upper surface 29 of the rotatable horizontal support portion 25 includes a grooved portion, or ring, 22 that is structured and arranged to be concentric and coaxial about the axis of rotation of the rotatable horizontal support portion 25. Preferably, the grooved portion 22 is dimensioned, e.g., width and depth, to accommodate at least one of a sealing unit 13, e.g., a ring gasket, sealing ring, O-ring, and the like, and the bottom lip 39 of the rotating portion 35 of the RETA 30, to provide a watertight seal. More preferably, the grooved portion 22 also includes a plurality of openings 28 that are disposed at discrete locations within the grooved portion 22. Most preferably, the plurality of openings 28 are structured and arranged to be in registration with the location of a plurality of corresponding openings 37a disposed in the bottom lip 39 of the rotating portion 35 of the RETA 30.

Any means for releasably securing or attaching the bottom lip 39 of the rotating portion 35 to the rotatable horizontal support portion 25 can be used. Preferably, tightening devices 38a, e.g., screws, Allen screws, bolts, clamps, and the like, can be used to releasably secure the rotating portion 35 and, optionally, a sealing device 13 to the rotatable horizontal support portion 25.

Although a preferred embodiment has been described to include a grooved portion 22 having a plurality of openings 28 for receiving tightening devices 38a, the invention is not to be limited thereto. For example, a grooved portion 22 is not necessary and, instead, the sealing device 13 can be applied to and disposed on the upper surface 29 of the rotatable horizontal support portion 25 instead of in a grooved portion 22. Furthermore, no sealing device 13 is necessary if the rotating portion 35 is already sealed at its bottom.

Furthermore, instead of a plurality of openings 28 for receiving tightening devices 38a, the rotatable horizontal support portion 25 can include a plurality of threaded vertical posts (not shown) that are structured and arranged concentrically and coaxially about the axis of rotation of the rotatable horizontal support portion 25 at discrete locations that are in registration with a similar plurality of corresponding openings 37a in the bottom lip 39 of the rotating portion 35 of the RETA 30. When the rotatable horizontal support portion 25 includes vertical posts instead of openings 28, the tightening devices 38a, preferably, are releasably attachable to the vertical posts. Representative examples of these tightening devices 38a can include, without limitation, one or more of nuts, washers, locking nuts, wing nuts, and the like instead of screw-type devices.

The purpose of the vertical support portion 23 is to support and stabilize the torque cell unit 40 and the non-rotating portion of the RETA 30. More specifically, the vertical support portion 23 supports and stabilizes the medium sample 7 during erosion rate testing. Preferably, the vertical support portion 23 includes a securing device 21 for releasably securing the torque cell unit 40 to the vertical support portion 23. Although the illustrative embodiment of the system 20 shown in FIG. 2 provides a securing device 21 that is disposed above the torque cell unit 40, it is equally acceptable to secure the torque cell unit 40 from a side, in which case the vertical support portion 23 would not need the support arm 24.

The Torque Cell Unit

Figure 4:
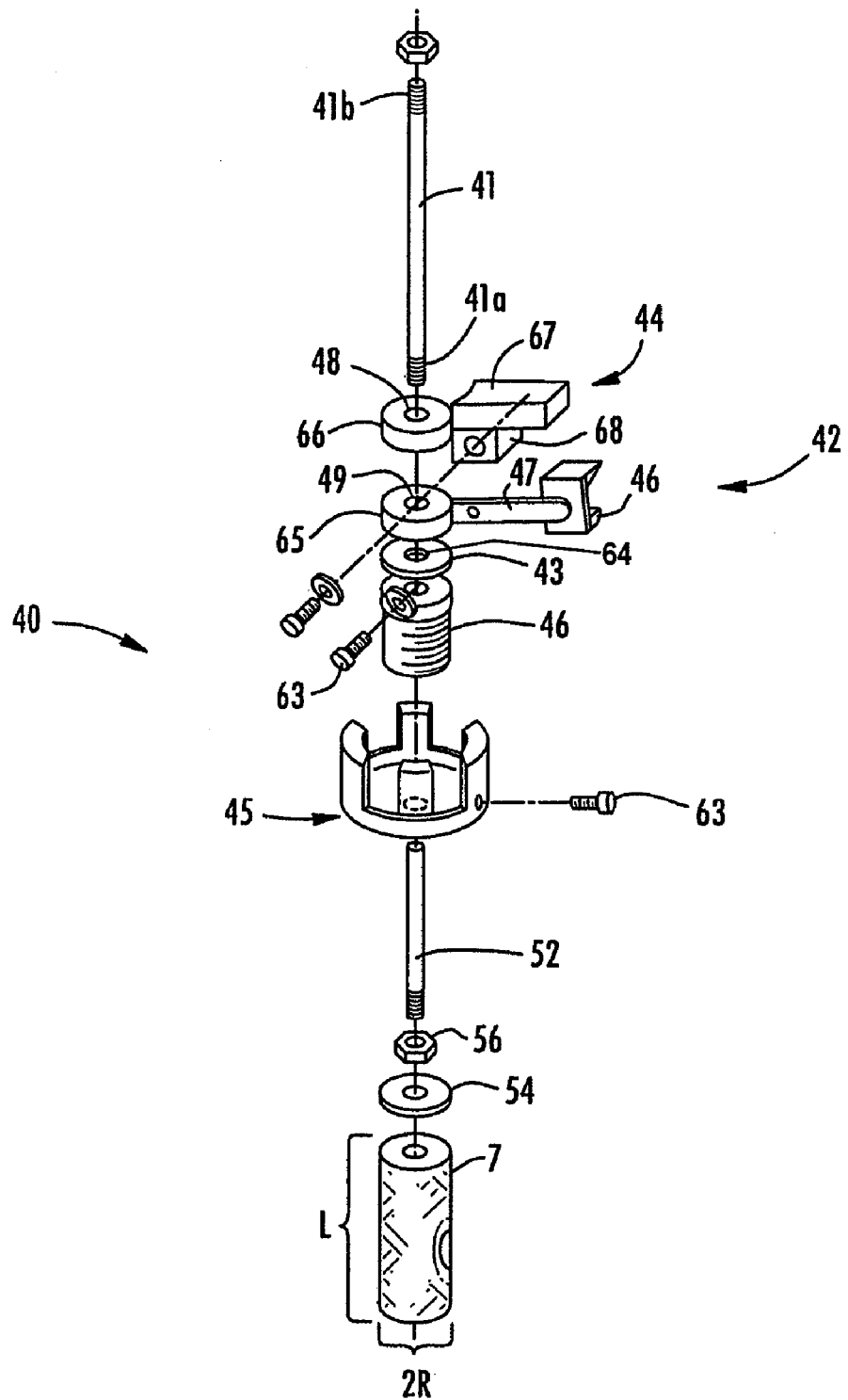
FIG. 4 is an exploded view of an illustrative embodiment of a torque cell unit in accordance with the present invention.

Referring to FIG. 4, a preferred embodiment of the torque cell unit 40 will now be described. FIG. 4 provides an exploded view of the torque arm 42 and mechanical stop 44, the upper, adjustable clutch slip unit 46, and lower clutch assembly 45, which comprise the major components of the torque cell unit 40.

In one aspect of the torque cell unit 40, the torque arm 42, mechanical stop 44, and upper, adjustable clutch slip unit 46 are structured and arranged on an upper support rod 41. More preferably, the distal end 41a of upper support rod 41 is disposed, successively, through an opening 48 in the mechanical stop 44, and opening 49 in the torque arm 42, and a hole (not shown) in the upper, adjustable clutch slip mechanism 46. In one aspect of the present invention, the distal end 41a of the upper support rod 41 includes a plurality of threads for removably attaching the distal end 41a of the upper support rod 41 to a plurality of corresponding threads in the hole of the upper, adjustable clutch slip mechanism 46. Optionally, to attach the upper, adjustable clutch slip mechanism 46 to the upper support rod 41 more securely, a locking means 63, e.g., a screw, Allen screw, bolt, and the like, can be used to frictionally engage the distal end 41a of the upper support rod 41 by tightening the locking means 63.

Optionally, one or more spacers 43 can be disposed between the upper, adjustable clutch slip mechanism 46 and the torque arm 42. Preferably, the one or more spacers 43 is cylindrically or disk shaped and includes an opening 64 through which the upper support rod 41 also can be disposed. The purpose of the space 43 is to provide a space between the upper, adjustable clutch slip mechanism 46 and the torque arm 42.

The purpose of the torque arm 42 is to measure the amount of torque applied to the medium sample 7 and to prevent damage to the sample 7 and/or the torque cell unit 40 in the event that an object, i.e., a piece of the medium sample, becomes lodged between the liner 34 and the medium sample 7, causing the sample to rotate along with the liner 34 and the rotating portion 35. Preferably, the slip torque, which will be discussed in greater detail below, is set at a torque value that is slightly higher than the maximum anticipated torque value under normal operation. Thus, if the measured torque exceeds the maximum anticipated torque value, the controller 26 can turn off the drive motor.

In a preferred embodiment, the torque arm 42 comprises a central portion 65, a moment arm portion 47, and a strain gage portion 46. Preferably, the central portion 65 is cylindrically or disk shaped and includes a coaxial, concentric, circular opening 49 through which the upper support rod 41 is disposed. More preferably, the moment arm portion 47 is fixedly attached to and extends radially outward from the outer periphery of the central portion 65. In one aspect of the torque arm 42, a strain gage 46 is fixedly attached to the end of the moment arm portion 47 to measure radial strain. Preferably, the strain gage is a bending beam type load cell of a type that is commercially available and well known to those skilled in the art.

In a preferred embodiment, the mechanical stop 44 comprises a central portion 66, an upper stop portion 67, and a torque arm support portion 68. The purpose of the mechanical stop 44 is to apply a slight pre-torque to the strain gage 46 to provide an additional safety feature behind the moment arm portion 47 and, also, to prevent the applied torque from exceeding the limiting force on the strain gage 46. Preferably, the central portion 66 is cylindrically or disk shaped and includes a coaxial, concentric, circular opening 48 through which the upper support rod 41 is disposed. More preferably, the upper stop portion 67 is fixedly attached to and extends radially outward from the outer periphery of the central portion 66. In one aspect of the mechanical stop 44, the torque arm support portion 68 is releasably attached to the moment arm portion 47 of the torque arm 42.

In another aspect of the torque cell unit 40, the lower clutch assembly 45 is in operational association with the adjustable clutch slip mechanism 46 and is releasably attached to the support rod 52 that also supports the medium sample 7 as described in greater detail below. Preferably, the distal end 55 of support rod 52 is disposed through a hole (not shown) in the lower clutch assembly 45. In one aspect of various embodiments of the present invention, the distal end 55 of the support rod 52 includes a plurality of threads for removably attaching the distal end 55 of the support rod 52 to a plurality of corresponding threads in the hole of the lower clutch assembly 45. Optionally, to attach the lower clutch assembly 45 to the support rod 52 more securely, a locking means 63, e.g., a screw, Allen screw, bolt, and the like, can be used to frictionally engage the distal end 55 of the support rod 52 by tightening the locking means 63.

The relative function of the adjustable clutch slip assembly 46 and the lower clutch assembly 45 will now be described. The adjustable clutch slip assembly 46 and the lower clutch assembly 45 provide "over-torque" protection for the medium sample 7 and the torque unit 40. Under normal operating conditions, the rotating portion 35 transfers shear stress to the outer surface of the stationary medium sample 7. The applied shear stress causes the sample 7 and the support rod 52 to rotate commensurate with the magnitude of the applied shear stress. Rotation of the sample 7 and support rod 52 is transferred to the strain gage 46 on the torque arm 44 via the adjustable clutch slip assembly 46 and the lower clutch assembly 45, which are in operational association with each other, and the upper support shaft 41.

In a preferred embodiment, the strain gage 46 has been calibrated to convert strain measurements of the strain gage 46 to the applied shear stress on the surface of the medium sample 7. Accordingly, direct, real time strain measurement data and indirect shear stress data can be transmitted to the controller 26 and stored in memory and/or used in calculations as needed.

Preferably, the maximum allowable torque in the adjustable clutch slip mechanism has been predetermined and preset so that should a portion of the medium sample 7 of sufficient size dislodge from the medium sample and cause the sample 7 to rotate with the liner 34 of the rotating portion 35, once the maximum allowable torque is exceeded, the adjustable clutch slip assembly 46 will disengage from the lower clutch assembly 45 to prevent further rotation of and/or damage to the medium sample 7. More preferably, in the event the adjustable clutch slip assembly 46 malfunctions, the mechanical stop 44 can be adjusted to signal the controller 26 to stop the motor driving the rotating portion 35 when the measured strain exceeds a predetermined maximum allowable strain.

The torque cell unit 40, and, more particularly, the strain gage 46 mounted on the torque arm 42, measures the torque, T, imparted to a medium sample 7 by the movement of the fluid in the liner 34. Knowing the radius, R, and the length, L, of the medium sample 7 and the measured torque from the strain gage 46 mounted on the torque arm 42, the average shear stress (z) on the surface of the sample 7 can be computed using the following equation.

$$\tau = AverageShearStress = \frac{T}{2\pi RL}$$

In a preferred embodiment of use, the rotating portion 35 can be rotated for a given period of time at a predetermined speed. This rotational energy will cause the fluid in the liner 34 to exert a shear stress over the outer surface of the medium sample 7. The applied shear stress, with time, will erode or dislodge some fraction of the medium sample. The eroded or dislodged material will either settle in the bottom of the liner 34 or will remain suspended in the rotating fluid.

Once the given period of time has expired, rotational energy to the rotating portion 35 will no longer be delivered, allowing the fluid in the liner 34 to come to a state of rest. Subsequently, the fluid- and material-containing liner 34 that is in a frictional fit with the rotating portion 35 can be removed from the rotating portion 35. The removed liner 34 will include the remaining fluid and any portions of the medium sample 7 that have been dislodged or otherwise eroded from the media sample 7 during the given period of time.

Preferably, the liner 34 containing the fluid can be weighed then oven-dried to remove the fluid completely. After the liner 34 and eroded medium material are "dry", the liner 34 can be weighed again. From this weight, the tare weight of the liner 34 can be subtracted to provide the "dry" eroded medium material from which one can determine the amount and percentage of mass and/or volume of the medium sample 7 lost due to the shear activity of the moving fluid, i.e., the mass of the medium sample 7 lost.

Alternatively, the fluid containing the eroded medium materials suspended therein, can be filtered to separate the fluid from the solid eroded medium material. To ensure that all of the eroded material is recovered in the filter element, the inside of the liner 34 can be washed a plurality of times until all of the visible eroded material is recovered in the filter.

The solid eroded medium material collected in the filter can then be oven-dried and the "dry" material can be weighed to provide a measure of the amount and percentage of mass and/or volume of the medium sample 7 lost due to the shear activity of the moving fluid, i.e., the mass of the medium sample 7 lost.

Knowing the mass of the material lost (Am) and the duration of the test (At) the average rate of erosion can be computed using the following equation.

$$\frac{\Delta r}{\Delta t} = \frac{\Delta m}{2\pi \rho RLD}$$

Where
$\Delta r$=change in radius of sample during test,
$\Delta t$=D=duration of the test,
$\Delta m$=mass removed from sample during test, and
$\rho$=dry mass density of the sample.

The Sample-Supporting Portion

Figure 5:
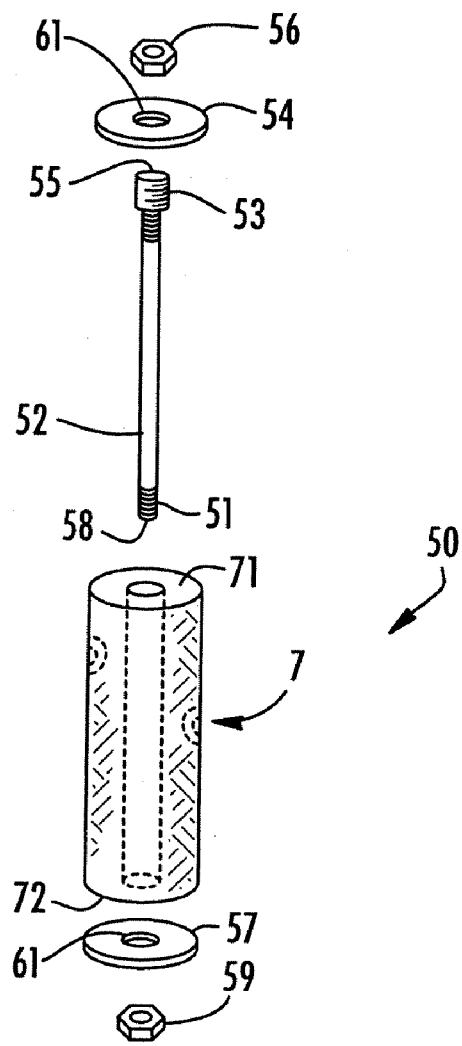
FIG. 5 is an exploded view of an illustrative embodiment of a sample-supporting portion for supporting a medium sample in accordance with the present invention.

The stationary portion—or non-rotating portion—of the system 20 includes the torque cell unit 40 described above and a sample-supporting portion 50. Referring to FIG. 5, the sample-supporting portion 50 of the system 20 will now be described. In a preferred embodiment, the sample-supporting portion 50 comprises a support rod 52, a top platen 54, a bottom platen 57, and top and bottom securing devices 56 and 59. Preferably, the support rod 52, typically fabricated from stainless steel or other non-corrosive metal, fiberglass or some other composite material, includes a diameter that is slightly smaller than the diameter of an opening that has been drilled or bored into the medium sample 7. In one embodiment, the support rod 52 is coated with Teflon®, manufactured by DuPont of Wilmington Del., for greater ease in inserting the support rod 52 into medium samples 7. Optionally, the support rod 52 can include threaded regions 51 and 53 that are disposed at a proximal end 58 and a distal end 55 of the support rod 52, respectively.

The sample-supporting portion 50 is structured and arranged to support and stabilize a medium sample 7 during testing and, moreover, to restrain or minimize movement of the medium sample 7 during the same. To this end, preferably, a top platen 54 and a bottom platen 57 are provided and structured and arranged to abut against and to frictionally engage, respectively, a top end 71 and a bottom end 72 of the medium sample 7. More preferably, the platens 54 and 57 are cylindrical in shape, e.g., disk-shaped, with a round opening 61 at the center of the cylindrical platens 54 and 57. The diameter of the round opening 61 should be just slightly larger than the diameter of the supporting rod 52 to allow easy assembly with minimal free-play or travel between the outer surface of the supporting rod 52 and the surface of the periphery of the inner diameter of the platens 54 and 57.

To provide confining pressures to the platens 54 and 57 for restricting movement of the medium sample 7, top and bottom securing devices 56 and 59 are needed. In a preferred embodiment, which is shown in FIG. 5, a top locking nut 56 and a bottom locking nut 59 are provided to ensure that the top and bottom platens 54 and 57 abut snugly against the upper and lower ends of the medium sample 71 and 72, respectively, without crushing or otherwise fracturing the medium sample 7. Preferably, the top locking nut 56 and a bottom locking nut 59 are releasably secured and tighten on the threaded regions 53 and 51 of the supporting rod 52.

Figure 5A:
FIGS. 5A-5C are alternative securing devices for use with the sample-supporting portion.
Figure 5B:
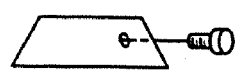
Figure 5C:
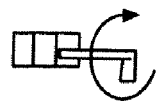

Those skilled in the art are aware of other means some that require threading, e.g., a thumb screw, a wing nut (FIG. 5A), and the like, and some that do not require threading, e.g., a locking key nut (FIG. 5B), a ring and screw device (FIG. 5C), and the like, that can be used besides a locking nut 56 and/or 59 to maintain a snug fit between the platens 54 and 57 and the ends of the medium sample 71 and 72.

The Rotating Portion of the RETA

Referring to FIG. 3, the rotating portion 35 of the RETA 30 will now be described. In a preferred embodiment; the rotating portion 35 comprises an outer cylinder 32, an insert 34, and a cover portion 36. Although the outer portion 32 of the rotation portion 35 is shown as a cylinder, other shapes, albeit less effective, could be used by those skilled in the art.

Preferably, the outer cylinder 32, which, for example, can be fabricated from cast acrylic; is open-at one end and closed at the other and, further, includes an upper lip 33 at the open end and a lower lip 39 at the closed end for operationally attaching the outer cylinder 32 to the cover portion 36 and the rotatable horizontal support portion 25, respectively. As previously disclosed, in one aspect of the present invention, the lower lip 39 of the outer cylinder 32 includes a plurality of corresponding openings 37a that are structured and arranged to be in registration with a plurality of openings 28 (or, alternatively a plurality of vertical posts) that are disposed in the rotatable horizontal support portion 25. Similarly, in another aspect of the present invention, the upper lip 33 includes a plurality of openings 37b that are structured and arranged at discrete locations about the outer periphery of the upper lip 33 to be in registration with a plurality of corresponding openings 37c disposed on the cover portion 36.

In a preferred embodiment, the cover portion 36 is a partially open, disk-shaped cylinder that is fabricated from a transparent or semi-transparent material, e.g., cast acrylic and durable, high temperature resistant materials. Preferably, the cover portion 36 is structured and arranged to provide a plurality of corresponding openings 37c near its outer periphery that are in registration with a plurality of openings 37b on the upper lip 33 of the outer cylinder 32. Once the plurality of openings 37b and 37c are properly aligned and in registration, securing devices 38b, e.g., screws, Allen screws, bolts, clamps and the like, can be installed in the openings to releasably attached the cover portion 36 to the outer cylinder 32. If the upper lip 33 includes vertical posts (not shown) in lieu of a plurality of openings 37c, then the securing devices 38b would include wing nuts (FIG. 5A), locking nuts, locking key nut (FIG. 5B), a ring and screw device (FIG. 5C), and the like.

Preferably, the cover portion 36 also includes a circular central opening 31 that is structured and arranged coaxially and concentrically about the axis of rotation of the rotating portion 35. The central opening 31 allows operators to view the medium sample 7 and, more particularly, to observe the level of the fluid during the various-phases of operation of the system 20 and to add additional fluid as necessary.

The Control Unit

Figure 6:
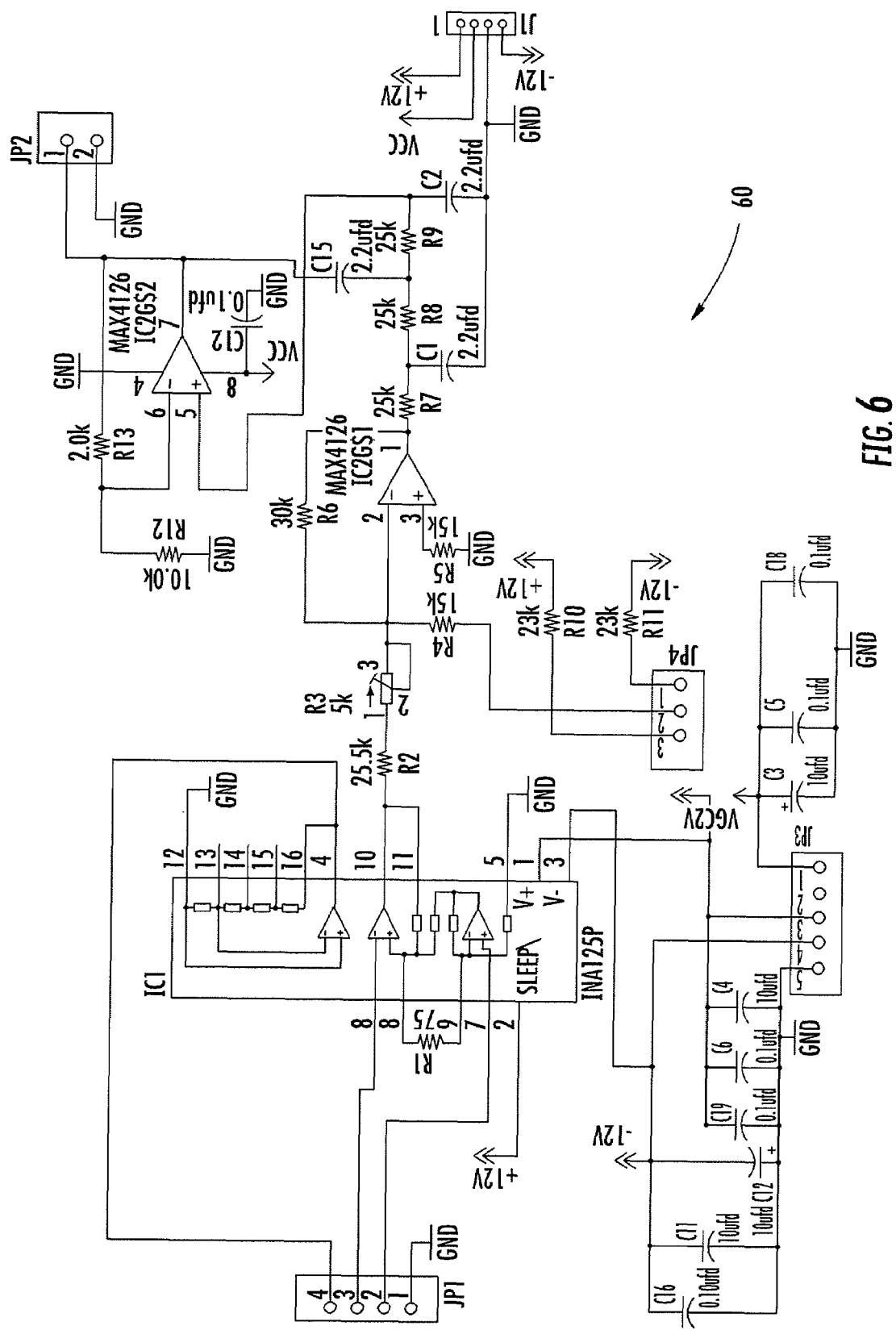
FIG. 6 is a circuit diagram of an illustrative embodiment of a control unit in accordance with the present invention.
Figure 7A:
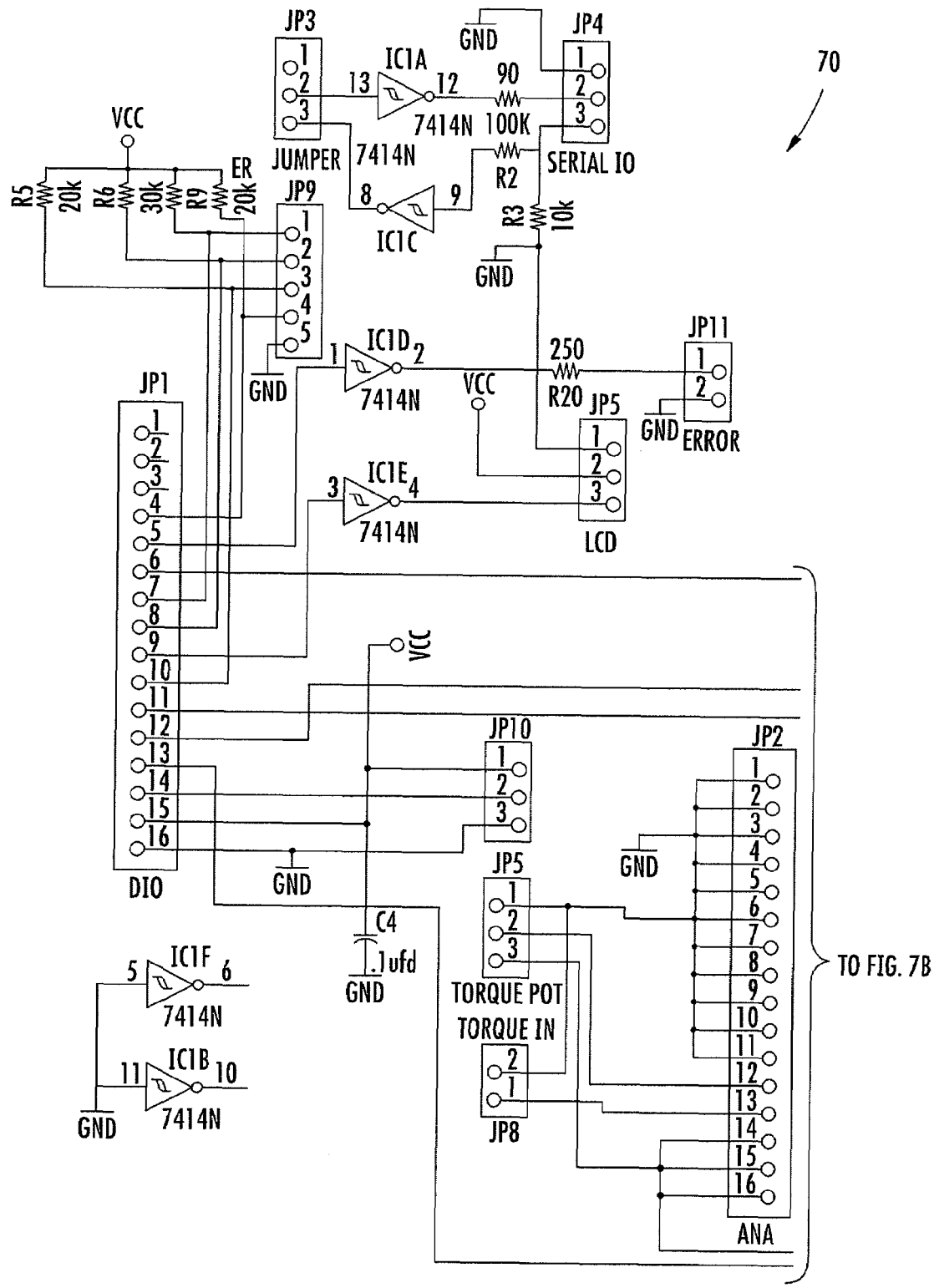
FIG. 7 is a circuit diagram of illustrative embodiment of an alternative control unit in accordance with the present invention.
Figure 7B:
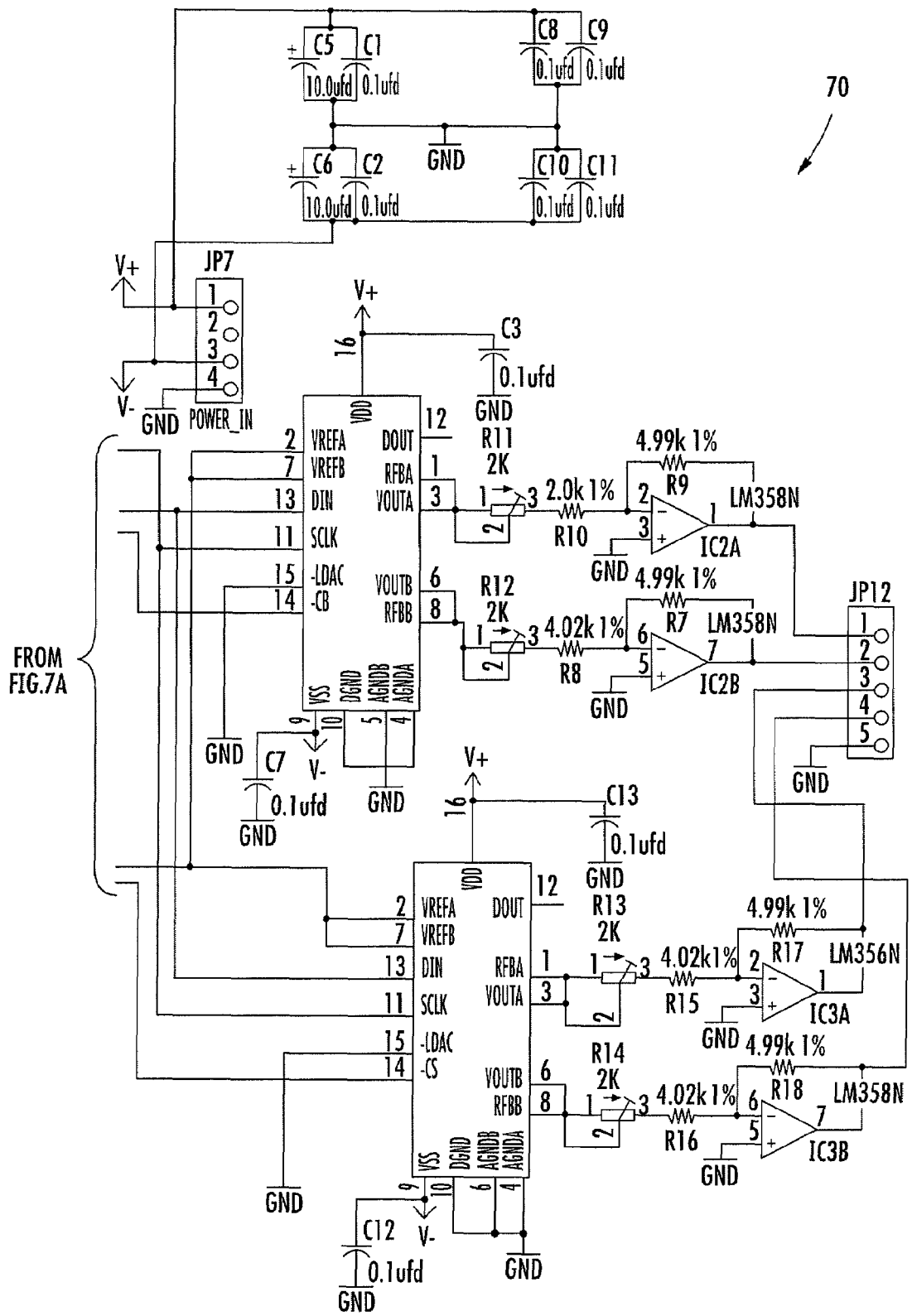

Referring to FIGS. 2, 6, and 7, embodiments of a control system 60 will be described. The control system 60 comprises a control unit 26 that performs control and data acquisition functions. For example, the control unit 26 can receive speed ("RPM") measurement data signals from the motor and torque measurement data signals from the load cell 46 and time data. These data can be stored in memory and, further, used to adjust the speed of the motor and/or the torque on the sample and to estimate shear stress on and rate of erosion of the medium sample. The control unit 26 also can process temperature measurements, which can be used to relate erosion rate to temperature.

Preferably, the control unit 60 allows either the torque or a rotational speed to be specified to the motor. When torque is specified, the control unit 26 increases the rotational speed of the outer cylinder 32 until the measured torque on the medium sample 7 (as measured by the load cell 46) reaches the desired, pre-determined level. The control unit 26 can maintain this torque until the given testing period is over, a change (increase or decrease) in torque is desired, or normal operations have been interrupted, e.g., by a dislodged piece of the medium sample 7.

In this "torque mode" if there is a change is anything that would impact the torque, e.g., a water temperature change, the rotating speed of the motor can be adjusted to maintain a constant or near constant torque.

Alternatively, in a rotational speed mode, the rotating speed of the motor is simply held at the desired constant value.

Makeup Fluid Supply System

In particular embodiments of the invention, the system includes an apparatus for replenishing fluid (e.g., water) within the liner 34 that, for example, evaporates over time. To accomplish this, in various embodiments, a drip system is provided for gradually supplying fluid (e.g., at a pre-determined rate) to the interior of the liner 34. In one embodiment, the fluid replenishment apparatus is adapted to provide a refrigerated supply of fluid (e.g., the fluid may be provided from a refrigerated container). In particular embodiments, re-supplying the liner 34 with refrigerated fluid serves to maintain the fluid within the liner at a pre-determined temperature (e.g., approximately 25 degrees Celsius). This may serve to offset a rise in the fluid temperature due to friction.

Sediment Sample Preparation and Test Procedure

Having described systems for evaluating the rate at which sediment erodes as a function of shear stresses applied by a flowing fluid and apparatuses for subjecting a medium sample to the shear stresses applied by a flowing fluid, methods of preparing samples for testing and for evaluating the rate at which sediment erodes as a function of shear stresses applied by a flowing fluid will be described.

Sample Preparation

Figure 8:
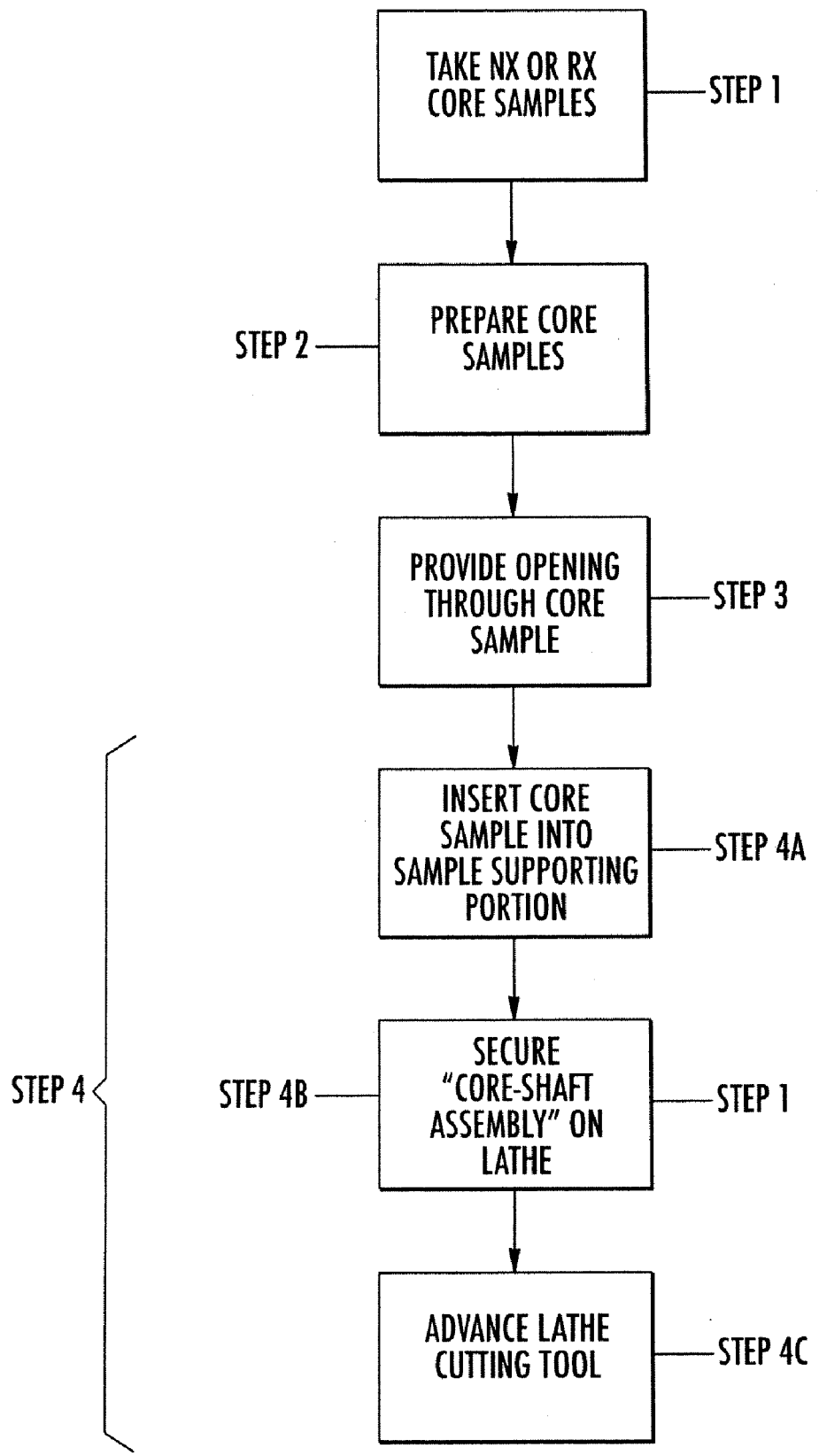
FIG. 8 is a flow chart of an embodied method of preparing a media sample for erosion testing.
Figure 12A:
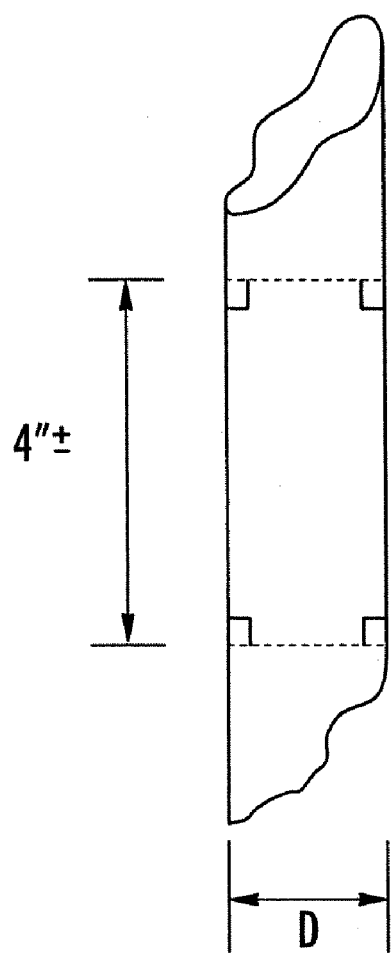
FIGS. 12A and 12B are diagrams of a typical rock core sample and a prepared medium sample, respectively.
Figure 12B:
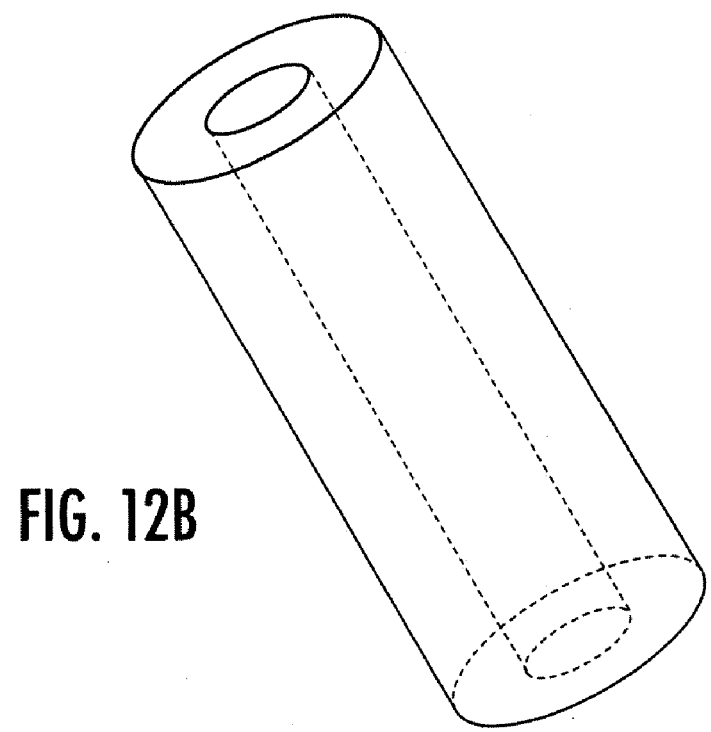

Referring to FIGS. 8, 12A, and 12B, a method of preparing a medium sample for erosion testing will now be described. In a preferred embodiment, samples of the medium to be tested will comprise cylindrically-shaped, drill core quality, medium samples having a nominal diameter of about 2⅛ inches (for NX core samples) or, alternatively, a nominal diameter of about 4 inches (for RX core samples) (STEP 1). Preferably, the medium sample to be tested will be prepared mechanically, e.g., using a wet saw of a type that is well-known to those skilled in the art, to provide a medium sample with a core length of about 4 inches and having planar or substantially planar 90° cut on the distal and proximal ends 71 and 72 of the medium sample (STEP 2). Optionally, the distal and proximal ends 71 and 72 of the medium sample can be polished to remove any asperities and the like to provide a planar or substantially planar surface.

Once the medium sample has been mechanically prepared, an opening through the length of the medium sample can be prepared (STEP 3). Preferably, the opening will have a nominal diameter of about 5/16 inch (for an RX-size media sample core) and will be prepared through the center axis of the medium sample. Although reference is made to an RX-size core sample, this is not to preclude other standard-size, e.g., NX sample, or non-standard size samples from being used.

For example, the medium sample can be disposed in a lathe chuck that has been modified expressly for securing and centering a medium sample in a drill press. In one embodiment, the drill chuck can be a modified three-prong lathe chuck of a type that is well known to those skilled in the art. The jaws of the lathe chuck should be tightened carefully to avoid fracturing the medium sample. Furthermore, if the medium sample is "out-of-round", the medium sample should be rotated until the jaws of the lathe chuck are not positioned over a localized high point. Preferably, the lathe chuck and the medium sample are centered along the axis of the drill bit of the drill press.

Once the medium sample and lathe chuck are properly positioned and releasably secured in place, boring operations can begin from either the distal or proximal ends of the medium sample. Preferably, the opening should be bored slowly, e.g., using a masonry drill bit, and in increments so that the opening and the drill bit can be cleared and cleaned often. More preferably, to prevent cracking or damaging of the medium sample, boring of the opening is advanced to about the mid-length of the medium sample.

Once the opening has been bored halfway through the medium sample from one of its ends, the medium sample is removed from the lathe chuck; inverted; and re-installed and releasably secured in the lathe chuck mark as described above. Preferably, before the medium sample is removed from the lathe chuck, an outline of the prongs of the lathe chuck can be provided on the outer surface of the medium sample so that, after the medium sample has been inverted and is being re-inserted in the lathe chuck, the prongs of the lathe chuck jaws can be re-positioned at or -substantially at the same location on the medium sample.

Subsequently, the lathe chuck and the medium sample are again centered along the axis of the drill bit of the drill press. Once the medium sample and lathe chuck are properly positioned and releasably secured in place, boring operations can begin from the other end of the medium sample. Here again, preferably, the opening should be bored slowly and in increments so that the opening and the drill bit can be cleared and cleaned often. The second boring operation is advanced until the second boring meets the first boring at the mid-length of the medium sample.

Having bored an opening through the entire length of the medium sample, the roundness of the sample can be tested (STEP 4). Preferably, a threaded rod can be installed through the opening in the medium sample. A pair of end platens can be disposed in contact with the distal and proximal ends of the medium sample and, further, releasably attached to the threaded, rod, e.g., using a nut that is compatible with the threaded portion of the supporting rod (STEP 4A).

In a preferred embodiment, one of the end platens includes a conical-shaped indention that is compatible with the live center on the lathe. The end platen with the conical-shaped indention should be disposed against the medium sample so that the conical-shaped indentation is oriented out or away from the medium sample. The medium sample so arranged will hereinafter be referred to as a "core-shaft assembly".

In a next step, the core-shaft assembly is operationally disposed in the lathe (STEP 4B). Preferably, the end platen without the indention can be inserted and releasably secured in the lathe chuck. More preferably, the end platen with the conical shaped indentation is inserted and releasably secured in the live center of the lathe.

Once the core-shaft assembly is properly secured in the lathe (STEP 4B), the lathe can be started and a cutting tool advanced along the outer periphery of the rotating medium sample (STEP 4C) to provide a medium sample with a true or approximately true diameter along its entire length. Preferably, the "out-of-roundness" of the finished medium sample should not exceed 1/32 inch. More preferably, however, removal of material from the outer periphery of the medium sample should provide or take the least cut possible.

Once the peripheral surface on the diameter of the medium sample is made uniform or substantially uniform over its entire length, the medium sample can be removed from the lathe and from the core-shaft assembly. Preferably, any loose debris from the lathing operation or the boring operations can be removed from the medium sample. More preferably, loose debris from the lathing or boring operations can be removed in accordance with the following, pre-testing procedure.

Pre-Testing Phase Operations

Figure 9:
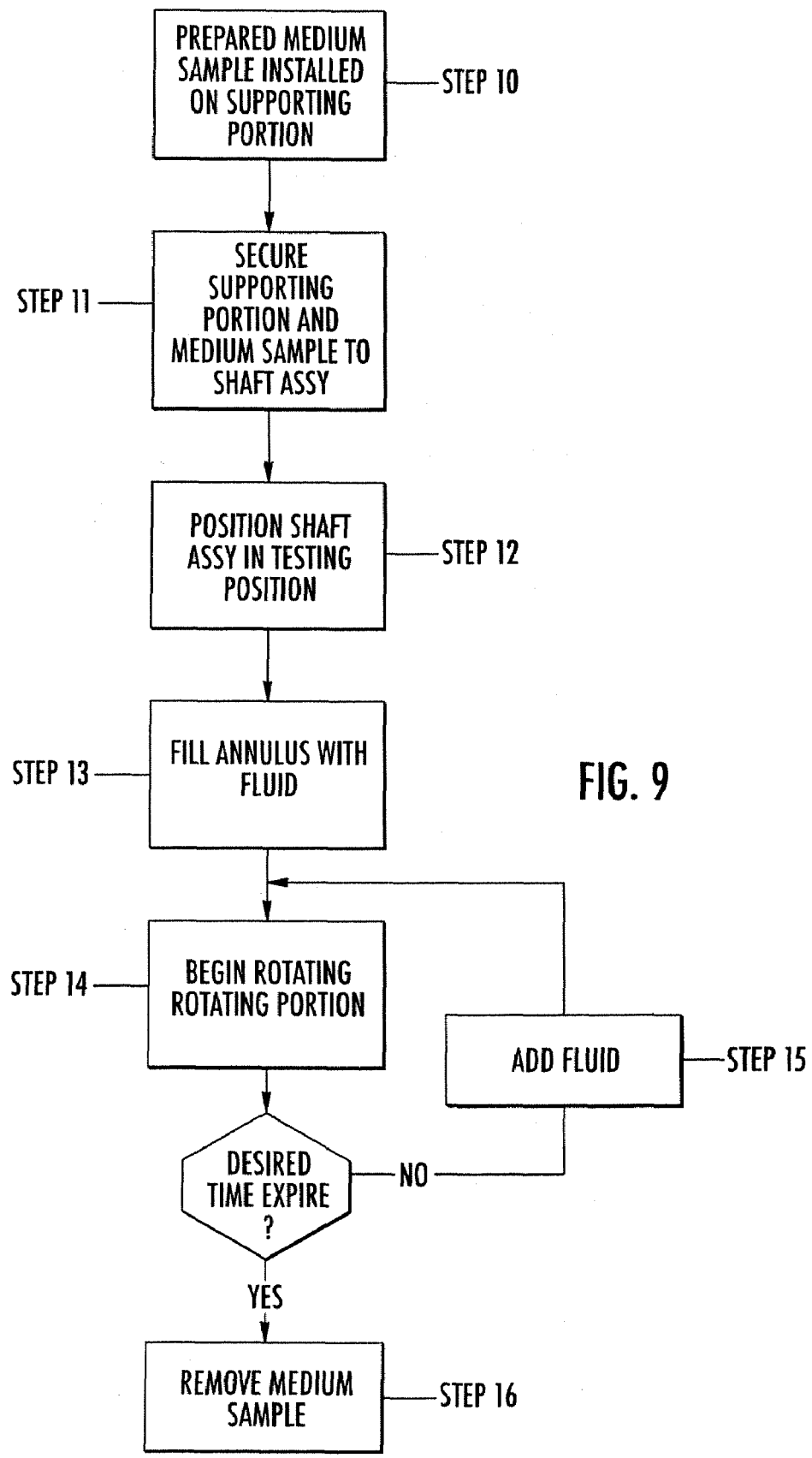
FIG. 9 is a flow chart of an embodied method of pre-testing and preparing 30 medium samples to establish a baseline of physical properties.

Having prepared a media sample and checked it for roundness, Pre-Testing phase operations can be performed to establish baseline parameters of the physical properties media sample. Referring to FIG. 9, first, the prepared medium sample is installed on the sample-supporting portion of the testing device (STEP 10) and the guide plate is moved to the top position on the slide-rail system. In a preferred embodiment, before the prepared medium sample is placed on the supporting rod, first, the cover for the rotating portion, the top nut, and the top platen are positioned, in that order; over the supporting rod. Subsequently, the prepared medium sample, the bottom platen, and the bottom nut can be positioned, in that order, over the support rod. Preferably, the bottom nut is positioned so that it is flush with the bottom of the supporting rod when tightened. More preferably, the sample is centered on the supporting rod so that the edges of the medium sample are flush or substantially flush with the edges of the top and bottom platens. Once the medium sample is properly centered, the medium sample can be releasably secured between the top and bottom platens, e.g., by tighten the top nut carefully.

In a second step, the supporting rod and the medium sample can be releasably secured to the shaft assembly (STEP 11) providing a "core-shaft assembly". Preferably, the support rod is releasably secured to the bottom of the guide plate housing.

In the next step, the guide plate and core-shaft assembly can then be lowered into the testing position in the rotating portion of the RETA and the guide plate can be locked in the testing position (STEP 12). Prior to lowering the core-shaft assembly into the rotating portion of the RETA, the insert should have already been inserted and should have been filled with the fluid to a height of approximately 1.5 inches (approximately 1/3 full). With the medium sample locked in the testing position, the lid of the rotating cylinder can be removably secured to the rotating cylinder using a securing device, e.g., Allen head screws, bolts, clamps, screws, and the like.

Additional fluid can then be introduced into the annulus between the inner periphery of the insert and the medium sample (STEP 13). Preferably, the fluid is introduced into the annulus between the inner periphery of the insert and the medium sample until the fluid reaches the upper surface of the top platen. Fluid can be introduced into the annulus through the circular opening in the cover portion of the rotating portion.

Once the medium sample has been releasable secured in the BETA and the annulus between the inner periphery of the rotating portion and the medium sample filled with fluid, the rotatable horizontal support portion to which the rotating portion is in operational, association can be rotated at a desired torque, at a desired speed, for desired period of time (STEP 14). Preferably, during the Pre-Testing phase of operation, the operating torque should be at or near the maximum operating torque to be used for testing the particular medium sample.

More particularly, when the ON button of the RETA Control Unit has been activated, the speed, i.e., RPM, of the rotating cylinder will increase at a controlled rate until the desired operating torque is reached. Once rotation of the rotating cylinder begins, there may be some loss in the level of the fluid. Accordingly, additional fluid should be added as needed throughout the Pre-Testing phase of operation. Preferably, the fluid level can be maintained to the upper rim of the top platen (STEP 15), so that the medium sample remains completely or substantially completely immersed throughout the Pre-Testing phase of operation.

In a preferred embodiment, the Pre-Testing phase of operation can be run continuously for about 15 to about 20 hours. Periodic torque measurements can be taken manually using a chronometer, e.g., a stopwatch, a watch, a timer or other time keeping instrument, or, more preferably, the process can be automated using a microprocessor, having a control processing unit, memory, input/output devices, and an internal clock, and an algorithm, e.g., a software program, that takes period torque measurement readings at specified times and/or at a specified time intervals; compares the measured torque level readings with the desired torque level; and adjusts the speed of the rotating portion to achieve the desired torque level.

At the completion of the speed Pre-Testing time period and after the RETA Control Unit has been manually turned OFF or, alternatively, has been turned OFF automatically by the aforementioned software algorithm and sufficient, time has passed to allow the fluid in the annulus to come to a stationary state, the medium sample can be removed from the supporting rod for Pre-Testing (STEP 16). More specifically, in a preferred embodiment, the cover portion can be removed, e.g., by using an Allen wrench, and the guide plate lifted and secured in the top position of the slide rail. The supporting rod and medium sample can then be removed carefully from the guide plate to avoid further volumetric loss of the medium sample.

More particularly, to remove the medium sample from the supporting rod (STEP 16), first the bottom nut and bottom platen can be removed, which will allow the medium sample to come off the bottom or proximal end of the support rod. Extreme care should be taken when removing the medium sample to avoid further volumetric loss or other damage to the medium sample Once the medium sample has been removed from the supporting rod, it can be rinsed to remove any loose material. Preferably, distilled water is the best rinse solution; however, depending on the medium sample, e.g., when the medium sample is an artificial material such as a ceramic or composite material, the rinse can also includes acids, bases, and the like. After the rinse, the Pre-Testing phase physical properties of the medium sample can be determined as described below.

Determination of Medium Sample Physical Properties

Figure 10:
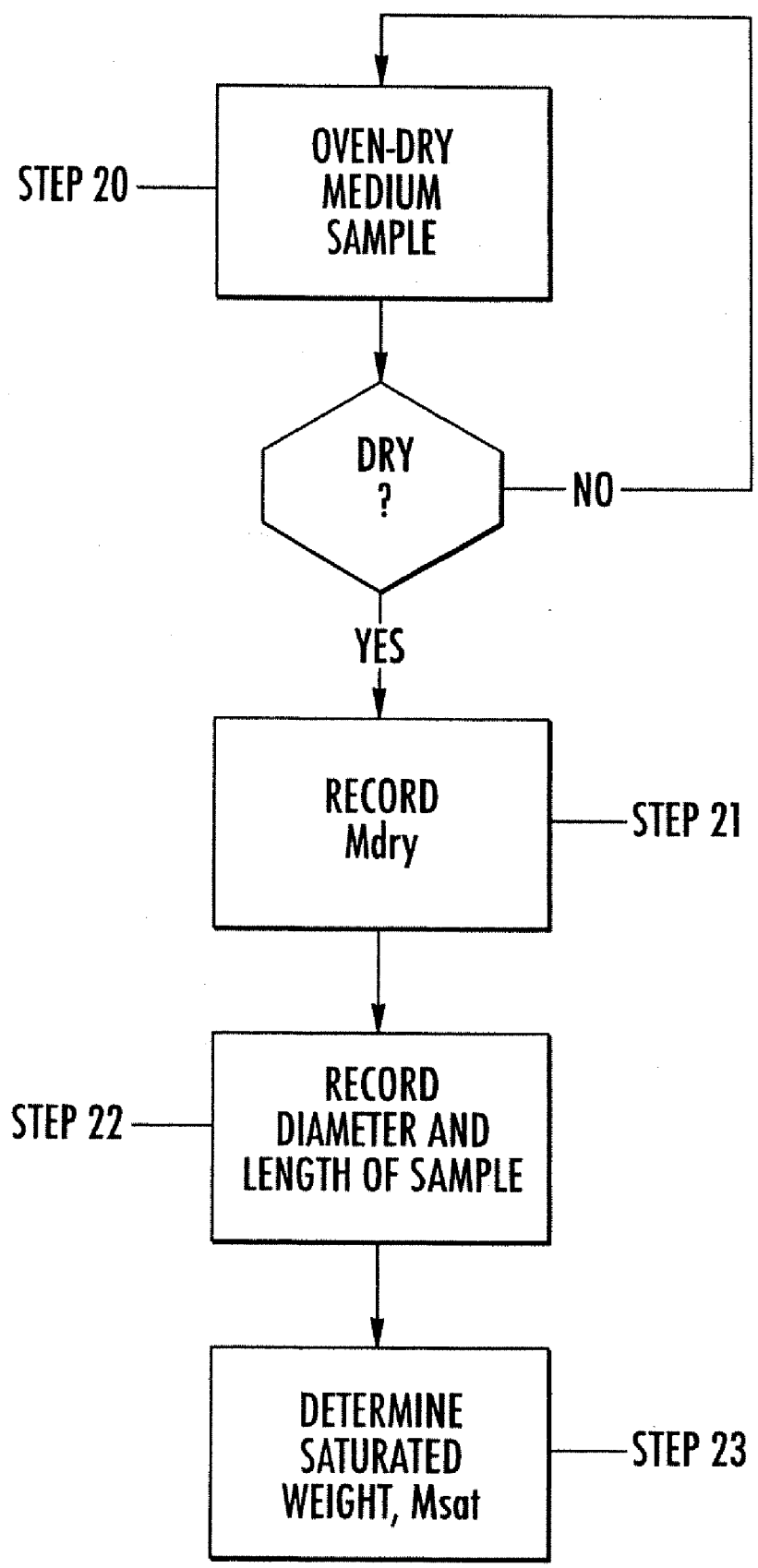
FIG. 10 is a flow chart of an embodied method of determining physical properties of the prepared medium sample.
Figure 11:
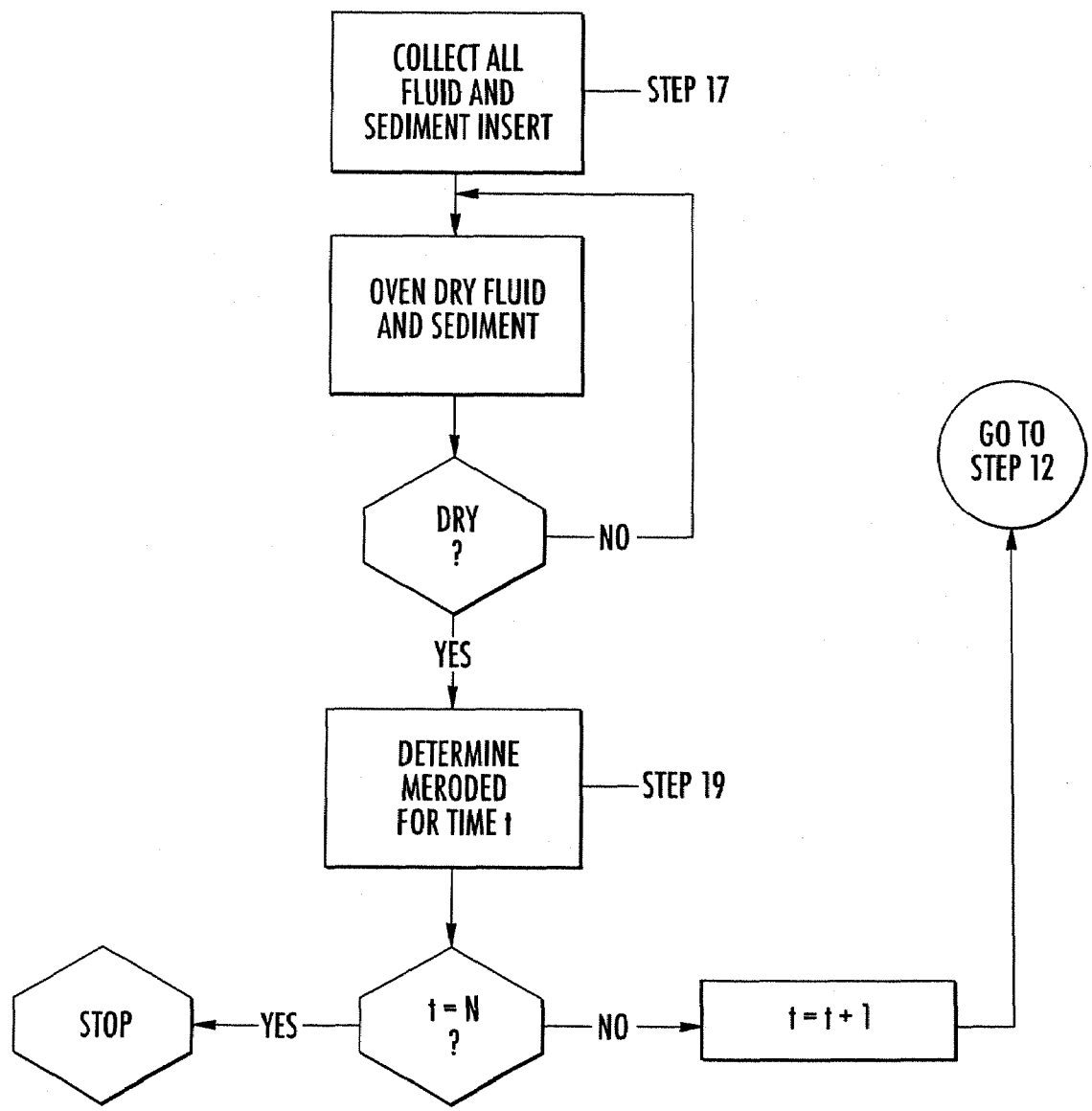
FIG. 11 is a flow chart of an embodied method of determining the rate of erosion of the prepared medium sample in accordance with the present invention.

Referring to FIG. 10, methods of determining physical properties of the prepared medium sample will now be described. Preferably, the physical properties of interest include the dry unit weight (or mass), the wet unit weight (or mass), the average diameter of the sample medium, and the average length of the sample medium.

Preferably, to determine the wet and dry unit masses of the medium sample, the prepared medium sample can weighed and then be placed in a drying oven that is capable of heating the prepared medium sample at a constant temperature of about 140° F. for a minimum of at least 16 hours or until the prepared medium sample is dry. The medium sample can be considered "dry" when the change in mass is less than about 0.1% during a period of one hour. More preferably, after about 15 hours in the oven and for every hour afterwards, the prepared medium sample can be removed from the oven and weighed using a precision balance that is accurate to +/−0.001 grams of a type and model—that is well known to those skilled in the art. Once the hourly mass change is less than 0.1%, the final sample dry mass, $m_{(dry)}$, can be recorded (STEP 21).

In a further step, the diameter and length of the "oven-dried" medium sample can be measured and recorded (STEP 22). Preferably, the diameter and length measurements are taken with calipers or a periphery measuring tape, e.g., PI® Tape manufactured by PI® Tape Corporation of Escondido, Calif. More preferably, the diameter and length of the medium sample are taken at a plurality of locations to estimate a mean value, a medium value, a range of values, and standard deviations of the medium sample. Most preferably, the diameter and length of the medium sample are taken at a minimum of three discrete locations. The mean value, medium value, a range of values, and standard deviations of the data can be calculated for the diameter and length of the medium sample.

Finally, the mass of the saturated medium sample can be calculated (STEP 23). In a preferred embodiment, a volume of water can be placed in a graduated container, e.g., a graduated cylinder, and the volume of the water, $V_{(water)}$ recorded. Preferably, sufficient water is placed in the graduated container initially so that the water will completely cover the medium sample when the medium sample is placed in the container and immersed in the water.

The "oven dried" medium sample can then be placed in the graduated container and immersed in the water contained therein. The volume of the water plus the dry sample, $V_{(water+dry\ sample)}$, can then be recorded. The graduated container can then be covered to minimize liquid loss through evaporation and, preferably, the medium sample can be left in a submerged state for a period of about 16 hours. After about 16 hours of submersion, the volume of water and saturated sample, $V_{(water+sat\ sample)}$ can be recorded. The saturated medium sample can then be removed from the graduated container, allowing excess water on the surface of the medium sample to fall from the sample back into the graduated container.

Once water ceases to form drips on the medium sample, the medium sample can be weighed, e.g., with a precision balance, and the mass of the saturated sample, $m_{(sat)}$, can be recorded (STEP 24). The recorded masses (dry and saturated), volumes, average diameter, and average length establish a baseline from which subsequent sediment erosion testing, which is described in the following section, can be evaluated.

Erosion Rate Testing Process

The first few steps of the Erosion Rate Testing Process are virtually the same as the Pre-Testing phase operation. Specifically, referring to FIG. 9, in a first step; the saturated medium sample can be installed on the sample-supporting portion of the testing device (STEP 10) and the guide plate is moved to the top position on the slide-rail system. In a preferred embodiment, before the prepared medium sample is placed on the supporting rod, first, the cover portion of the rotating portion, the top nut, and the top platen are positioned, in that order, over the supporting rod. Subsequently, the saturated medium sample, the bottom platen, and the bottom nut can be positioned, in that order, over the supporting rod.

Preferably, the bottom nut is positioned so that it is flush with the bottom of the supporting rod when tightened. More preferably, the saturated medium sample is centered on the supporting rod so that the edges of the medium sample are flush or substantially flush with the edges of the top and bottom platens. Once the medium sample is properly centered, the medium sample can be releasably secured between the top and bottom platens, e.g., by tighten the top nut carefully.

In a subsequent step, the support rod and the medium sample and supporting portion can be releasably secured to the shaft assembly (STEP 11). Preferably, the supporting rod is releasably secured to the bottom of the guide plate housing.

The guide plate and core-shaft assembly sample can then be lowered into the testing position in the rotating portion of the RETA and the guide plate can be locked in the testing position (STEP 12). Prior to lowering the core-shaft assembly into the rotating portion of the RETA, the insert should have already been inserted and should have been filled with the fluid to a height of approximately 1.5 inches (approximately ⅓ full). With the medium sample locked in the testing position, the cover portion of the rotating portion can be removably secured to the rotating cylinder using a securing device, e.g., Allen head screws, bolts, clamps, screws, and the like.

The fluid can then be introduced into the annulus between the inner periphery of the insert and the medium sample (STEP 13). Preferably, the fluid is introduced into the annulus between the insert and the medium sample until the fluid reaches the upper surface of the top platen. Fluid can be introduced into the annulus through an opening in the center of the lid of the rotating cylinder.

Once the medium sample has been releasable secured in the rotating cylinder and the annulus between the inner periphery of the rotating cylinder and the medium sample filled with fluid, the rotatable horizontal support portion to which the rotating portion is in operational association can be rotated at a desired torque, at a desired speed, for desired period of time (STEP 14). Preferably, during the Erosion Rate Testing phase of operation, the operating torque should be at or near the maximum operating torque.

For example, initially, "engineering judgment" is required in the selection of an operating torque to be used during the Erosion Rate testing phase. Those of ordinary skill in the art appreciate that the more erodable the material being tested, the lower the maximum applied torque should be and vice versa. Exemplary operating torques and test durations are provided in Tables 1 and 2 for 2⅛-inch and 4-inch medium samples, respectively. These values can be used as a starting point for most medium samples. Practitioners should, however, adjust them up or down to account for local conditions and so forth if there are indications that the medium is particularly scour resistant or easily eroded.

TABLE 1

Test torques and testing durations for 2.4" Diameter Samples

| Material | Pre-Test Torque per Duration (N mm/hr) | 3 Test Torques (N mm) | 5 Test Torques (N mm) | Test Duration (hrs) |
| --- | --- | --- | --- | --- |
| Stiff Clays | 7/1 | 20, 15, 10 | 20, 17, 14, 11, 8 | 3-6 |
| Soft Rock | 20/12 | 30, 20, 10 | 35, 25, 20, 15, 10 | 40 |
| Hard Rock | 25/15 | 40, 30, 20 | 45, 35, 25, 20, 15 | 72 |

TABLE 2

Test torques and testing durations for 4" Diameter Samples

| Material | Pre-Test Torque per Duration (N mm/hr) | 3 Test Torques (N mm) | 5 Test Torques (N mm) | Test Duration (hrs) |
| --- | --- | --- | --- | --- |
| Stiff Clays | 10/1 | 32, 40, 16 | 32, 28, 22, 18, 14 | 3-6 |
| Soft Rock | 32/12 | 48, 32, 16 | 56, 40, 32, 40, 16 | 40 |
| Hard Rock | 40/15 | 72, 52, 32 | 72, 56, 40, 32, 40 | 72 |

More particularly, when the ON button of the RETA Control Unit has been activated, the speed, i.e., RPM, of the rotating portion will increase at a controlled rate until the desired operating torque is reached. Once rotation of the rotating cylinder begins, there may be some loss in the level of the fluid. Accordingly, additional fluid should be added as needed throughout the Erosion Rate Testing phase of operation. Preferably, the fluid level can be maintained to the upper rim of the top platen (STEP 15), so that the medium sample remains completely or substantially immersed throughout the Erosion Rate Testing phase of operation.

In a preferred embodiment, the Erosion Rate Testing phase of operation can be run continuously for a plurality of cycles ("N") having periods ranging between about 40 hours (for soft rock and stiff soil samples) to about 72 hours (for harder rock samples). Preferably, each medium sample is tested for a minimum of at least three cycles and, more preferably, for a minimum of at least five cycles. Those skilled in the art will appreciate that the testing periods can be longer or shorter than the values provided herein without violating the scope or spirit of this disclosure. Unlike the Pre-Testing phase, however, during the Erosion Rate Testing phase, the duration of the experiment in minutes ($\Delta$(time)) can be measured and recorded and, also, the temperature of the fluid can be measured, e.g., with a thermometer, and recorded.

Preferably, the temperature of the fluid remains constant. However, the friction of the fluid on the medium sample will heat up the fluid. Accordingly, advantageously, a cool fluid source can be in fluid communication with the fluid in the insert so that when the controller detects an increase in temperature, cool fluid can be slowly added to maintain the fluid at a constant or near constant temperature. Preferably, the operation of the Erosion Rate Testing can be checked hourly, for the first three (3) hours, and then periodically thereafter. For example, periodically, i.e., at least every 12 hours, the apparatus should be checked for any changes in sound, appearance, vibration, water level, and overall behavior.

As previously mentioned, the clutch unit is variably adjustable. Preferably, it can be set to "break" at a predetermined torque level. More preferably, a plurality of plates are disposed between the top and the bottom portion of the clutch shaft that the top portion of the shaft can rotate independently from the bottom portion of the shaft when the predetermined torque value is exceeded and the clutch unit "breaks".

If there is an unusual vibration or sound coming from the testing apparatus, the test can be stopped by pressing the OFF button on the control unit. As provided in our description of the apparatus above, the Control Unit can shut down the BETA automatically if, for example, the measured torque exceeds a limiting value such as will occur if a piece of the medium sample is dislocated from the whole and lodges between the medium sample and the rotating cylinder. Optionally, one or more accelerometers can be removably attached to some portion or portions of the RETA to provide vibration data to the Control Unit so that, if the measured vibration levels exceed a pre—determined threshold vibration level, the motor can be shut off. Torque measurements can be automated using a plurality of sensors that provide signals of torque measurements, a microprocessor, having a control processing unit, memory, and input/output devices, and an algorithm, e.g., a software program, that takes periodic torque measurement readings at specified times and/or at a specified time intervals at specified time intervals; compares the measured torque level readings with the desired torque level; and adjusts the speed of the rotating cylinder to achieve the desired torque level.

At the completion of the speed Erosion Rate Testing time period and after the RETA Control Unit has been manually turned OFF or, alternatively, turned OFF automatically by the aforementioned software algorithm and sufficient time has passed to allow the fluid in the annulus to come to a stationary state, the insert in the rotating cylinder containing sediment from the medium sample can be collected and tested to evaluate changes in physical properties (STEP 17). The final temperature of the water, $Temp_{(end)}$, can also be measured, e.g., with the thermometer, at this point and recorded.

In a preferred embodiment, the cover portion can be removed from the outer portion of the rotating portion, e.g., using an Allen wrench, wrench, screwdriver, and the like; the guide plate lifted partially to an intermediate position so that the medium sample just clears the top of the fluid surface in the insert. At this intermediate location, the guide plate can be releasably secured on the slide rail. With the medium sample so disposed; residual water and eroded materials suspended in the same on the surface of the medium sample can drip off the medium sample and be collected in the insert. Then, once the medium sample has ceased dripping and all or substantially all of the excess eroded material has accumulated and been collected in the insert, the guide plate can be fully raised to the top position of the slide rail and releasably secured thereat.

The medium sample can now be removed from the sample-supporting portion (STEP 16) so that loose material adhering to it and/or the components of the sample-supporting portion can be rinsed and the loose material in the rinse wash collected in the insert. More particularly, to remove the medium sample, first the bottom nut and bottom platen can be removed, which will allow the medium sample to come off the bottom or proximal end of the support rod. Extreme care should be taken when removing the medium sample to avoid further volumetric loss or other damage to the medium sample.

Once the medium sample has been removed from the supporting rod, it can be rinsed to remove any loose material. Preferably, distilled water is the best rinse solution. But, once again, the rinse can include acids and bases when the medium sample is an artificial medium, e.g., ceramic, composites, and the like. The supporting rod, the platens and the nuts can also be rinsed to remove any loose material adhering to their outer surfaces as well. The rinsing solution and the material suspended therein should be collected in the insert.

The pre-weighed insert ($m_{insert}$) containing all of the collected sediment can then be removed from the rotating portion. It is important that no spillage of fluids occurs because eroded material from the medium sample will be suspended in the fluid so any loss of fluid will likely result in a loss of eroded material as well, which can lead to an underestimation of erosion loss rate.

In a next step, the insert (or drying dish) containing the accumulated sediment can be placed in a drying oven that is set to a temperature of about 140° F. and heated to evaporate the fluid (STEP 18). In a preferred embodiment, the pre-weighed insert containing the collected sediment is placed in an oven. Optionally, the liquid and solid contents of the insert can be placed in a drying dish of known mass, $m_{dish}$. Preferably, before placing the contents of the insert into the drying dish, the fluid in the insert can be stirred to suspend additional material, i.e., sediment or adsorbed material, from the wetted, inner surface of the insert. More preferably, the insert can also be rinsed, e.g., using a wash or spray bottle containing a rinse solution, and the rinse solution also collected in the drying dish, to remove all solid material, i.e., sediment and adsorbed material, from the inner surface of the insert.

Preferably, the insert (or drying dish) and accumulated sediment can be heated for at least 16 hours until "dry". The sediment sample is considered "dry" when the change in mass is less than 0.1% in a period greater than one hour. Similar to the Pre-Test phase, after about 15 hours in the oven, the sediment sample can be weighed with a precision balance periodically, e.g., at least hourly. Once the sediment sample is "dry", the dry mass of the insert (or drying dish) and accumulated material, $m_{(insert+eroded)}$ (or $m_{(dish+eroded)}$), can be recorded and the dry mass of the accumulated material, $m_{(eroded)}$, calculated (STEP 19).

From these measurements, one skilled in the art can determine the total mass loss of the medium sample, which can be empirically related to time, temperature, and other parameters to evaluate the Erosion Rate of the medium sample and, ultimately, the medium samples suitability as a foundation material. At a minimum, the rate of erosion of each medium sample should is measured for a minimum of three (arid preferably five) cycles ("N") of applied shear stresses. This repetition will provide sufficient data to determine and plot Erosion Rate versus Shear Stress relationships and the like.

The invention has been described in detail including preferred embodiments thereof. However, modifications and improvements within the scope of this invention will occur to those skilled in the art. The above description is intended to be exemplary only. The scope of this invention is defined only by the following claims and their equivalents.

For example, although the invention has been described for use in connection with rock and soil samples, the invention can also be used for testing virtually any self-supporting medium, e.g., ceramic, cement, concrete, and the like.

What we claim is:

1. A system for evaluating a rate of erosion of a medium sample subject to shear stresses generated by movement of a fluid, the system comprising:
   a rotating erosion testing apparatus (RETA) that includes:
   a rotating portion, having an upper opening, that contains a fluid for providing a desired torque or a desired shear stress to the medium sample through the fluid;
   a support portion for supporting and stabilizing the medium sample during testing, that can be inserted into and removed from the upper opening of the rotating portion to a desired position in said rotating portion;
   a torque cell and clutch unit for measuring an operating torque imparted to the medium sample disposed on the support portion;
   a vertical support portion for supporting and stabilizing the support portion and the torque cell unit of the rotating erosion testing apparatus;
   a horizontal support portion, having an axis of rotation, for supporting and providing rotation to the rotating portion and to the fluid contained therein; and
   a control unit for controlling the torque or shear stress applied to the rotating portion and the medium sample.

2. The system as recited in claim 1, wherein the medium is a core sample of rock, a core sample of a hard or stiff cohesive soil, ceramic, concrete or cement.

3. The system as recited in claim 1 wherein the fluid is selected from the group consisting of fresh water, salt water, oil, an acidic solution, a saline solution, a slurry mixture, glycerin, and any liquid exhibiting high viscosity.

4. The system as recited in claim 1, wherein the torque cell and clutch unit is stabilized so that it does not rotate.

5. The system as recited in claim 1, wherein the rotating portion further comprises a cover portion that is releasably attachable to the rotating portion to cover some portion of the opening in said rotating portion.

6. The system as recited in claim 1, wherein the rotating portion further comprises a removable insert for holding and retaining the fluid and any material that dislodges from the medium sample during testing.

7. The system as recited in claim 1, wherein the horizontal support portion includes a grooved portion that is structured and arranged concentrically and coaxially about the axis of rotation and, further, dimensioned to accommodate the rotating portion of the rotating erosion testing apparatus.

8. The system as recited in claim 7, wherein the grooved portion includes at least one of a plurality of openings and a plurality of vertical posts that are structured and arranged about said grooved portion to be in registration with a plurality of corresponding openings disposed on the rotating portion of the rotating erosion testing apparatus for the purpose of releasably attaching said rotating portion to the horizontal support portion.

9. The system as recited in claim 7, wherein the grooved portion is structured and arranged so that a sealing unit can be removably inserted in and releasably attached to said grooved portion for providing a watertight seal to the fluid that is contained in the rotating portion of the RETA.

10. The system as recited in claim 1, wherein the rotatable horizontal support portion includes at least one of a plurality of openings and a plurality of vertical posts that are structured and arranged concentrically and coaxially about the axis of rotation of said rotatable horizontal support portion to be in registration with a plurality of corresponding openings disposed on the rotating portion of the rotating erosion testing apparatus for the purpose of releasably attaching said rotating portion to said rotatable horizontal support portion at an upper surface thereof.

11. The system as recited in claim 10, wherein the upper surface of the rotatable horizontal support portion and the rotating portion of the rotating erosion testing apparatus are structured and arranged so that a seating unit can be removably inserted there between for providing a watertight seal to the fluid that is contained in said rotating portion.

12. The system as recited in claim 1, wherein the sample-supporting portion includes:
    a supporting rod having a diameter that is slight less than a diameter of an opening drilled or bored through the center of the medium sample;

a top platen, having a central opening that is structured and arranged to be slightly larger in diameter than the diameter of the support rod, for frictionally engaging an upper end of the media sample;

a bottom platen, having a central opening that is structured and arranged to be slightly larger in diameter than the diameter of the support rod, for frictionally engaging a lower end of the media sample; and a pair of securing devices for releasably securing the top platen and the bottom platen so that the medium sample is rigidly confined between the top and bottom platens.

13. The system as recited in claim 12, wherein the support rod is threaded at its proximal and distal ends for receiving a threaded tightening device.

14. The system as recited in claim 12, wherein the sample-supporting portion further includes a pair of gaskets, each of which is disposed between the medium sample and each of the top and bottom platens.

15. The system as recited in claim 1, wherein the torque cell and clutch unit comprises:

an upper clutch slip mechanism that is in operational association with a strain gage that is structured and arranged on a torque arm; and a lower clutch assembly that is in operational association with the medium sample, wherein the upper clutch slip mechanism can be set with a predetermined torque so that when a torque that is greater than the predetermined torque is applied to the lower clutch assembly, the system will shut down to stop the torque applied to said lower clutch assembly.

16. The system as recited in claim 15, wherein the torque cell and clutch unit comprises:

a strain gage that is structured and arranged on a torque arm for providing strain data that can be used to evaluate the shear stress applied to the medium sample by the rotating fluid.

17. The system as recited in claim 16, wherein the torque cell and clutch unit further comprises a mechanical stop that is structured and arranged in operational association with the torque arm so that if a torque that is greater than the predetermined torque is applied to the lower clutch assembly but the system does not shut down, the mechanical stop will cause the system to shut down.

18. The system as recited in claim 1, wherein the torque cell and clutch unit comprises:

a strain gage that is structured and arranged on a torque arm for providing strain data that can be used to evaluate the shear stress applied to the medium sample by the rotating fluid.

19. The system as recited in claim 18, wherein the strain gage is a bending beam load cell.

20. The system as recited in claim 1; wherein the control unit controls torque or shear stress applied to the rotating portion and the medium sample using strain measurement data from a strain gage mounted on a torque arm of the torque cell and clutch unit.

21. A testing apparatus for subjecting a medium sample to a moving fluid to evaluate a rate of erosion of the medium sample due to shear stresses generated by the moving fluid, the apparatus comprising:

a rotating portion, having an upper opening, that contains a fluid for providing a desired torque or a desired shear stress to the medium sample through the fluid;

a sample-supporting portion for supporting and stabilizing the medium sample during testing, that can be inserted into and removed from the upper opening of the rotating portion to a desired position in said rotating portion; and a torque cell and clutch unit for measuring an operating torque imparted to the medium sample disposed on the support portion.

22. The testing apparatus as recited in claim 21, wherein the medium is a core sample of rock or a core sample of a hard or stiff cohesive soil.

23. The testing apparatus as recited in claim 21 wherein the fluid is selected from the group consisting of fresh water, salt water, , a slurry mixture, glycerin, and any liquid exhibiting high viscosity.

24. The testing apparatus as recited in claim 21, wherein the torque cell and clutch unit is stabilized so that it does not rotate.

25. The testing apparatus oil, an acidic solution, a saline solution as recited in claim 21, wherein the rotating portion further comprises a cover portion that is releasably attachable to the rotating portion to cover some portion of the opening in said rotating portion.

26. The testing apparatus as recited in claim 21, wherein the rotating portion further comprises a removable insert for holding and retaining the fluid and any material that dislodges from the medium sample during testing.

27. The testing apparatus as recited in claim 21, wherein the rotating portion is structured and arranged to be attachable to an upper surface or a grooved portion of a rotatable horizontal support that supports and rotates the rotating portion.

28. The testing apparatus as recited in claim 27, wherein the grooved portion includes at least one of a plurality of openings and a plurality of vertical posts that are structured and arranged about said grooved portion to be in registration with a plurality of corresponding openings disposed on the rotating portion for the purpose of releasably attaching said rotating portion to the horizontal support portion.

29. The testing apparatus as recited in claim 27, wherein the rotating portion and grooved portion are structured and arranged so that a sealing unit can be removably inserted there between to provide a watertight seal to the fluid that is contained in said rotating portion.

30. The testing apparatus as recited in claim 21, wherein the sample-supporting portion includes:

a supporting rod having a diameter that is slightly less than a diameter of an opening drilled or bored through the center of the medium sample;

a top platen, having a central opening that is structured and arranged to be slightly larger in diameter than the diameter of the support rod, for frictionally engaging an upper end of the media sample;

a bottom platen, having a central opening that is structured and arranged to be slightly larger in diameter than the diameter of the support rod, for frictionally engaging a lower end of the media sample; and a pair of securing devices for releasably securing the top platen and the bottom platen so that the medium sample is rigidly confined between the top and bottom platens.

31. The testing apparatus as recited in claim 30, wherein the support rod is threaded at its proximal and distal ends for receiving a threaded tightening device.

32. The testing apparatus as recited in claim 30, wherein the sample-supporting portion further includes a pair of gaskets, each of which is disposed between the medium sample and each of the top and bottom platens.

33. The testing apparatus as recited in claim 21, wherein the torque cell and clutch unit comprises:

an upper clutch slip mechanism that is in operational association with a strain gage that is structured and arranged on a torque arm; and a lower clutch assembly that is in operational association with the medium sample, wherein the upper clutch slip mechanism can be set with a predetermined torque so that when a torque that is greater than the predetermined torque is applied to the lower clutch assembly, the testing apparatus will shut down to stop the torque applied to said lower clutch assembly.

34. The testing apparatus as recited in claim 33, wherein the torque cell and clutch unit comprises:

a strain gage that is structured and arranged on a torque arm for providing strain data that can be used to evaluate the shear stress applied to the medium sample by the rotating fluid.

35. The testing apparatus as recited in claim 33, wherein the torque cell and clutch unit further comprises a mechanical stop that is structured and arranged in operational association with the torque arm so that if a torque that is greater than the predetermined torque is applied to the lower clutch assembly but the testing apparatus does not shut down, the mechanical stop will cause the testing apparatus to shut down.

36. The testing apparatus as recited in claim 21, wherein the torque cell and clutch unit comprises:

a strain gage that is structured and arranged on a torque arm for providing strain data that can be used to evaluate the shear stress applied to the medium sample by the rotating fluid.

37. The testing apparatus as recited in claim 36, wherein the strain gage is a bending beam load cell.

38. The testing apparatus as recited in claim 21, wherein the control unit controls torque or shear stress applied to the rotating portion and the medium sample using strain measurement data from a strain gage mounted on a torque arm of the torque cell and clutch unit.

39. A method of testing and evaluating a rate of erosion of a medium sample subject to shear stresses generated by movement of a fluid, the method comprising:

providing a rotating erosion testing apparatus that includes:

a rotating portion, having an upper opening, that contains a fluid for providing a desired torque or a desired shear stress to the medium sample through the fluid;

a support portion for supporting and stabilizing the medium sample during testing, that can be inserted into and removed from the upper opening of the rotating portion to a desired position in said rotating portion;

a torque cell and clutch unit for measuring an operating torque imparted to the medium sample disposed on the support portion;

applying rotational energy to the rotating portion of the rotating erosion testing apparatus for a predetermined period of time;

measuring strain that is applied to the medium sample by the fluid in the rotating portion;

measuring an amount of weight loss or volume loss of the medium sample at the end of the predetermined period of time; and calculating a rate of erosion based on the weight loss or volume loss of the medium sample and said predetermined period of time.

40. The method as recited in claim 39, wherein the method further includes:

controlling the rotational energy applied to the rotating portion of the rotating erosion testing apparatus using strain data.

41. The method as recited in claim 39, wherein the method further includes:

monitoring a torque applied to the medium sample;

comparing the monitored torque with an allowable torque;

interrupting the rotational energy applied to the rotating portion of the rotating erosion testing apparatus when the monitored torque exceeds the allowable torque.

42. The method as recited in claim 39, wherein the method further includes:

monitoring a strain applied to the medium sample;

comparing the monitored torque with an allowable strain;

interrupting the rotational energy applied to the rotating portion of the rotating erosion testing apparatus when the monitored strain exceeds the allowable strain.

* * * * *

UNITED STATES PATENT AND TRADEMARK OFFICE
CERTIFICATE OF CORRECTION

PATENT NO. : 7,647,821 B2  Page 1 of 1
APPLICATION NO. : 12/053936
DATED : January 19, 2010
INVENTOR(S) : David G. Bloomquist and Donald Max Sheppard It is certified that error appears in the above-identified patent and that said Letters Patent is hereby corrected as shown below:

Column 22, line 9 in Claim 23, "water, , a slurry" should read --water, oil, an acidic solution, a saline solution, a slurry--; and Column 22, lines 14 to 15 in Claim 25, delete "oil, an acidic solution, a saline solution" from the claim.

Signed and Sealed this

Tenth Day of August, 2010

David J. Kappos
*Director of the United States Patent and Trademark Office*